United States Patent
Gustafsson et al.

(10) Patent No.: US 8,030,511 B2
(45) Date of Patent: Oct. 4, 2011

(54) METHOD FOR THE MANUFACTURE OF THERAPEUTIC COMPOUNDS AND COMPOSITIONS, COMPOUNDS AND COMPOSITIONS PRODUCED THEREWITH, AND THEIR USE

(76) Inventors: Lars E. Gustafsson, Hasselby (SE); Dag Linnarsson, Stocksund (SE); Kristofer Nilsson, Huskvarna (SE)

( * ) Notice: Subject to any disclaimer, the term of this patent is extended or adjusted under 35 U.S.C. 154(b) by 60 days.

(21) Appl. No.: 12/282,878

(22) PCT Filed: Mar. 14, 2007

(86) PCT No.: PCT/SE2007/050152
§ 371 (c)(1),
(2), (4) Date: Dec. 17, 2008

(87) PCT Pub. No.: WO2007/106034
PCT Pub. Date: Sep. 20, 2007

(65) Prior Publication Data
US 2009/0258944 A1    Oct. 15, 2009

(30) Foreign Application Priority Data
Mar. 14, 2006  (SE) ...................................... 0600566

(51) Int. Cl.
*C07C 203/04*   (2006.01)
(52) U.S. Cl. .................................................... 558/488
(58) Field of Classification Search .................... 558/488
See application file for complete search history.

(56) References Cited

U.S. PATENT DOCUMENTS
5,646,181 A * 7/1997 Fung et al. .................... 514/506

FOREIGN PATENT DOCUMENTS
| DE | 2144420 | 3/1973 |
| EP | 0911316 B1 | 1/2004 |
| WO | WO-96/38136 A1 | 12/1996 |
| WO | WO 2006102071 A1 * | 9/2006 |

OTHER PUBLICATIONS

Boruwa, et al. Tetrahedron Letters 46 (2005) 1743-1746.*
Nickerson, et al. Isobutyl nitrite and Related Compounds, published by Pharmex, Ltd (1979).*
International Search Report mailed Jul. 9, 2007, for PCT Application No. PCT/SE2007/050152 filed Mar. 14, 2007, 6 pages.
International Written Opinion mailed Jul. 9, 2007, for PCT Application No. PCT/SE2007/050152 filed Mar. 14, 2007, 8 pages.
European Search Report mailed Nov. 2, 2009, for EP application No. 07716121 filed Oct. 14, 2008, 7 pages.
Grossi et al. (Oct. 29, 1999). "A new synthesis of alkyl nitrites: the reaction of alkyl alcohols with nitric oxide in organic solvents," *J Org Chem* 64(22):8076-9.

* cited by examiner

*Primary Examiner* — Shawquia Young
(74) *Attorney, Agent, or Firm* — Morrison & Foerster LLP

(57) ABSTRACT

Organic nitrites can be produced from a compound which is a mono/polyhydric alcohol or an aldehyde- or ketone-derivate thereof after de-aeration of the same, using NO gas, and stored in an environment saturated with gaseous NO. Organic nitrites produced according to the invention exhibit less impurities and improved storage stability compared to conventionally produced nitrites. The organic nitrites of the invention can easily be formulated into pharmaceutical compositions and have utility for the treatment of various conditions.

3 Claims, 19 Drawing Sheets

Figure 1:
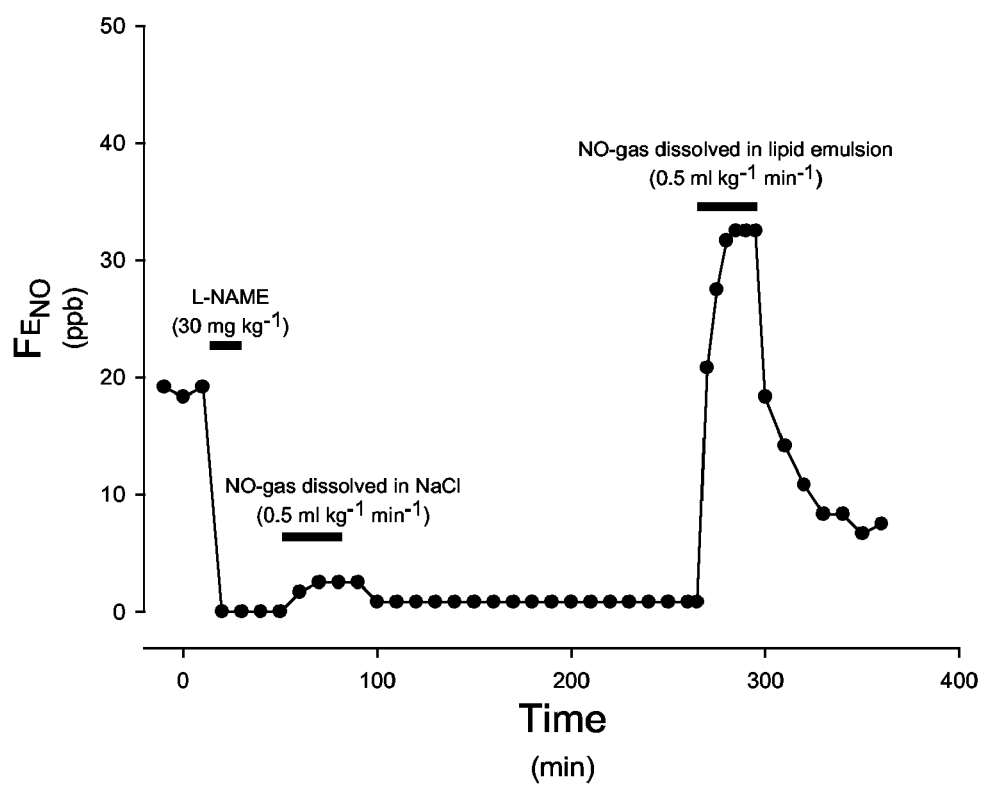

On-column inj.:
1 uL NO-treated propanol
100%
diluted 1:1 in toluene

METHOD FOR THE MANUFACTURE OF THERAPEUTIC COMPOUNDS AND COMPOSITIONS, COMPOUNDS AND COMPOSITIONS PRODUCED THEREWITH, AND THEIR USE

CROSS REFERENCE TO RELATED APPLICATIONS

This patent application is a U.S. National Phase application of PCT/SE2007/050152 filed Mar. 14, 2007, which claims priority to Sweden Application No. 0600566-4 filed Mar. 14, 2006, the contents of which are hereby incorporated by reference in the present disclosure in their entirety.

The present invention relates to a method for the production of compounds capable of generating or releasing gaseous nitric oxide in vivo, in particular organic nitrites, as well as pharmaceutical compositions or formulations comprising said compounds. Said compounds or compositions exhibit improved properties, such as improved stability, enhanced physiological acceptance and reduced side effects. The invention also relates to compounds and compositions obtainable by said method, as well as their use for the manufacture of pharmaceutical preparations. The invention also relates to methods for the treatment of various diseases and conditions, including the administration of said compounds or pharmaceutical compositions to a patient in need thereof.

BACKGROUND

Nitric Oxide

Nitric oxide (NO) is a molecule of importance in several biological systems, and is continuously produced in the lung and can be measured in ppb (parts per billion) in expired gas. The discovery of endogenous NO in exhaled air, and its use as a diagnostic marker of inflammation dates back to the early 1990-ies (See the published international patent applications WO 93/05709 and WO 95/02181). Today, the significance of endogenous NO is widely recognized, and since a few years back, a clinical analyzer is available on the market (NIOX®(, the first tailor-made NO analyzer for routine clinical use with asthma patients, AEROCRINE AB, Solna, Sweden).

The American Thoracic Society (ATS) has published guidelines for clinical NO measurements (American Thoracic Society, Medical Section of the American Lung Association Recommendations for standardized procedures for the online and offline measurement of exhaled lower respiratory nitric oxide and nasal nitric oxide in adults and children—1999, in *Am J Respir Crit Care Med*, 1999; 160:2104-2117).

It is generally recognised that endogenous generation of the gaseous NO molecule plays an important role in the modulation of pulmonary vascular tone to optimise ventilation-perfusion matching (Persson et al. 1990). In healthy human adults, NO is of importance in regulation of both basal pulmonary and systemic vascular resistance (Stamler et al. 1994). Local regulation of blood flow is influenced by administration of NO synthase inhibitor in healthy human subjects (Rimeika et al 2004). Vasodilator effects of endogenous NO in the postnatal pulmonary circulation clearly contribute to the adaptations of the fetal lung to air breathing at delivery (Abman et al. 1990). NO generation in the postnatal lung is stimulated for example by mechanical stretch, increased shear forces and increased $O_2$ tension in the alveoli (Heymann 1999). Measuring NO in exhaled breath is a good way of monitoring changes in endogenous NO production or scavenging in the lung (Gustafsson et al. 1991).

Further, U.S. Pat. No. 5,670,177 discloses a method for treating or preventing ischemia comprising administering to a patient by an intravascular route a gaseous mixture comprising NO and carbon dioxide $CO_2$ wherein the NO is present in an amount effective to treat or prevent ischemia.

U.S. Pat. No. 6,103,769 discloses a similar method, with the difference that saline, saturated with NO, is used.

The published international application WO 94/16740 teaches the use of NO delivering compounds, such as S-nitrosothiols, thionitrites, thionitrates, sydnonimines, furoxans, organic nitrates, nitroprusside, nitroglycerin, iron-nitrosyl compounds, etc, for the treatment or prevention of alcoholic liver injury.

Nitrates are presently used to treat the symptoms of angina (chest pain). Nitrates work by relaxing blood vessels and increasing the supply of blood and oxygen to the heart while reducing its workload. Examples of presently available nitrate drugs include:

Nitroglycerin (glyceryl nitrate) (1,2,3-propantriol-nitrate), which is today mostly taken sublingually to curb an acute attack of angina. Strong headaches and dizzyness due to the rapid and general vasodilatory effect are frequently encountered side-effects. Nitroglycerin infusion concentrates are also available, and diluted in isotonic glucose or physiological saline for intravenous infusion. Tolerance development is a problem both in acute and in long-term treatment regimens.

Isosorbide mononitrate (1,4:3,6-dianhydro-D-glucitol-5-nitrate), which is taken as prophylactic against angina pectoris. Tolerance development is a problem in long-term treatment regimens. Frequent side-effects include headache and dizziness, as encountered with nitroglycerin.

Isosorbide dinitrate (1,4:3,6-dianhydro-D-glucitol-2,5-nitrate), which is taken both acutely and prophylactically against angina pectoris and cardiac insufficiency.

Pentaerythrityl nitrates, a group of organic nitrate, are known to exert long-term antioxidant and anti-atherogenic effects by as yet unidentified mechanisms. Pentaerythrityl tetranitrate has been investigated in the context of nitrate tolerance, an unwanted development in nitrate therapy, and experimentally tested in pulmonary hypertension.

A number of compounds, glyceryl trinitrate, ethyl nitrite, isobutyl nitrate, isobutyl nitrite, isoamyl nitrite and butyl nitrite, have been tested in vivo and found to generate NO (Cederqvist et al., 1994). Significant correlation was obtained between in vivo generation of NO and effects on blood pressure in a rabbit model.

Accordingly, it has been suggested in U.S. Pat. No. 5,646, 181 that certain organic nitrites traditionally synthesized, have utility in treating male impotence and erectile dysfunction through topical or intracavernosal administration to the penis.

Inorganic nitrates and nitrites, such as potassium nitrite and sodium nitrite, have a long use as food preservatives. Nitrates and nitrites have in general been considered to be potentially harmful, due to the theoretically possible formation of carcinogenic N-nitroso compounds in food, and in humans in vivo. Lately, the role of dietary nitrates and nitrites has been re-evaluated, in particular as the endogenous production of NO in the arginine-nitric oxide system and its role in host defence has been discovered (Larsen et al., Effects of dietary nitrate on blood pressure in healthy volunteers, N Engl J Med 355, 2792-3 (2006)).

Finally, L-arginine, and esters thereof, such as the ethyl-, methyl- and butyl-L-arginine have been used to increase the endogenous production of NO.

WO 96/38136 discloses nitrosation of proteins using gaseous nitric oxide under anaerobic conditions, forming nitric oxide adducts used to coat the surfaces of devices to be introduced into the human body. Related patents are U.S. Pat. No. 6,352,709 and international patent publication WO 96/35416.

Among the compounds and compositions presently available, many are associated with undesired properties or side-effects, such as toxicity problems, stability problems, delayed action, irreversible action or prolonged action, etc. One particular problem, frequently encountered when administering a NO-donating compound in the form of an infusion, is the production of methemoglobin (metHb).

One objective behind the present invention was to develop improved methods for the production and handling of NO-donating compounds, such as organic nitrites, and the production or formulation of pharmaceutical preparations containing such compounds. Known organic nitrites and their therapeutic use are frequently associated with problems likely to be due to impurities and degradation products present in the compositions. It is also difficult to prepare pharmaceutical formulations containing organic nitrites, as the mixing steps and vehicles used may trigger further degradation. Similarly, due to the reactive properties of NO, the storage properties of such formulations are often less than satisfactory.

Another objective was to identify new methods and compositions for the delivery of NO, without the side effects or tolerance development associated with conventional treatments and drugs.

Another objective was to identify and synthesize novel NO-donating compounds.

Other objectives, the solutions reached and the advantages associated therewith will become evident upon study of the description and examples.

SUMMARY OF THE INVENTION

The present inventors have developed a novel method of synthesizing and handling organic nitrites, as well as handling conventionally synthesized organic nitrites, as disclosed in the description, examples and claims, hereby incorporated by reference.

The invention also makes available compounds and compositions consisting of or comprising organic nitrites, exhibiting advantageous properties compared to conventionally synthesised and formulated compounds and compositions, as well as their use for the treatment of various indications, where NO is believed to exert a beneficial influence. In particular, the invention makes available two novel NO-donors having the formulas I and II below:

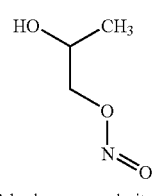

2-hydroxypropyl nitrite

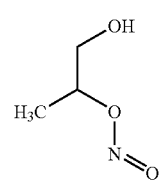

2-hydroxy-1-methylethyl nitrite

The invention also makes available an improved storage form for organic nitrites, preventing or at least significantly delaying their decomposition. Further aspects of the invention will become apparent to a skilled person upon study of the description, examples, claims and drawings.

Although specific features of the invention are mentioned in some embodiments and not in others, this is for convenience only as each feature may be combined with any other or all of the other features in accordance with the invention.

SHORT DESCRIPTION OF THE DRAWINGS

The present invention will be described in closer detail in the following description, examples and attached drawings, in which FIG. 1 is a graph showing changes in mixed exhaled nitric oxide ($FE_{NO}$) in an artificially-ventilated pentobarbital anaesthetised rabbit upon infusions of NO-gas dissolved in either saline or lipid emulsion in an animal with inhibited endogenous NO-production (L-NAME 30 mg kg$^{-1}$). The horizontal bars show the infusion times.

Figure 2:
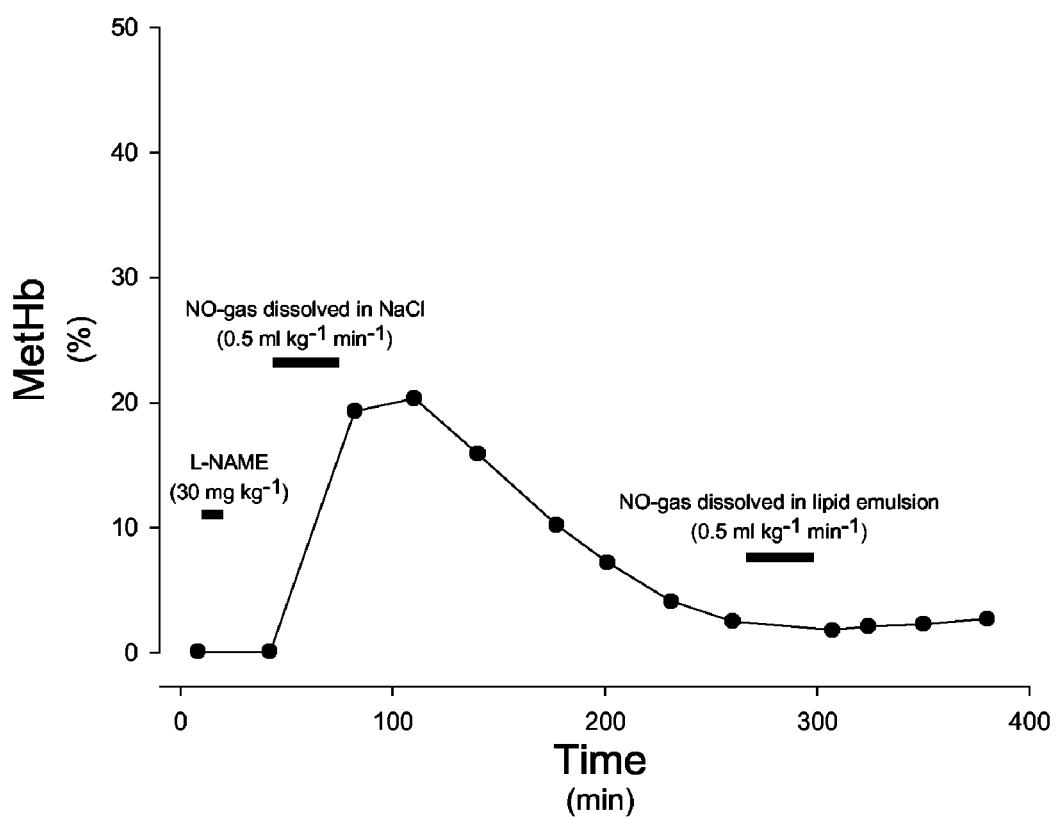

FIG. 2 is a graph showing changes in methemoglobin (MetHb) in arterial blood in an artificially-ventilated pentobarbital anaesthetised rabbit upon infusions of NO-gas dissolved in either saline or lipid emulsion in an animal with inhibited endogenous NO-production (L-NAME 30 mg kg$^{-1}$). The horizontal bars show the infusion times.

Figure 3:
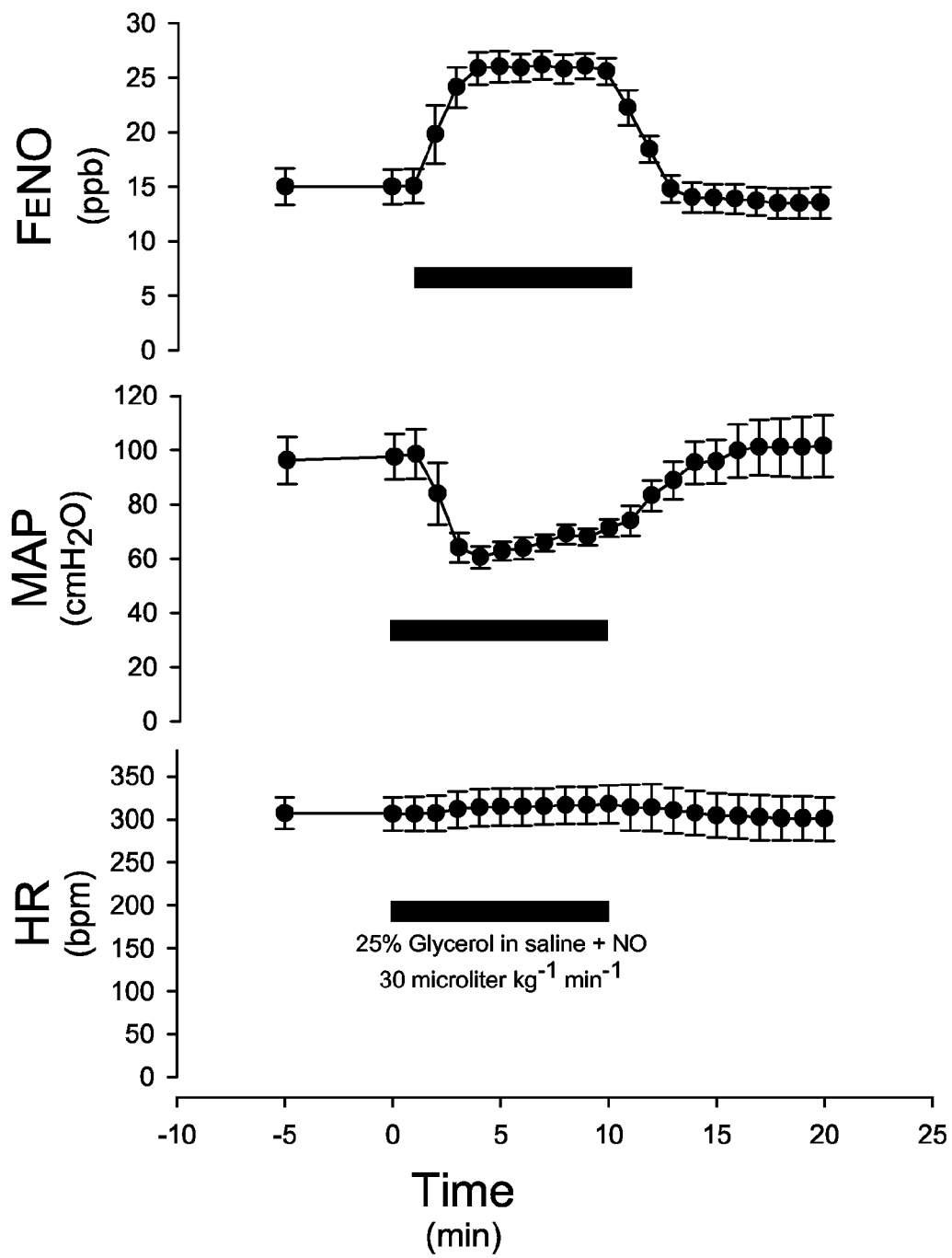

FIG. 3 consists of three graphs relating to experiments with artificially ventilated pentobarbital anesthetized rabbits (n=4-5). The graph shows the changes in mixed exhaled nitric oxide ($FENO$), mean arterial blood pressure (MAP) and heart rate (HR) due to intravenous infusion (30 microliter kg$^{-1}$ min$^{-1}$) of 25%-glycerol-NO. The horizontal bars show the infusion times.

Figure 4:
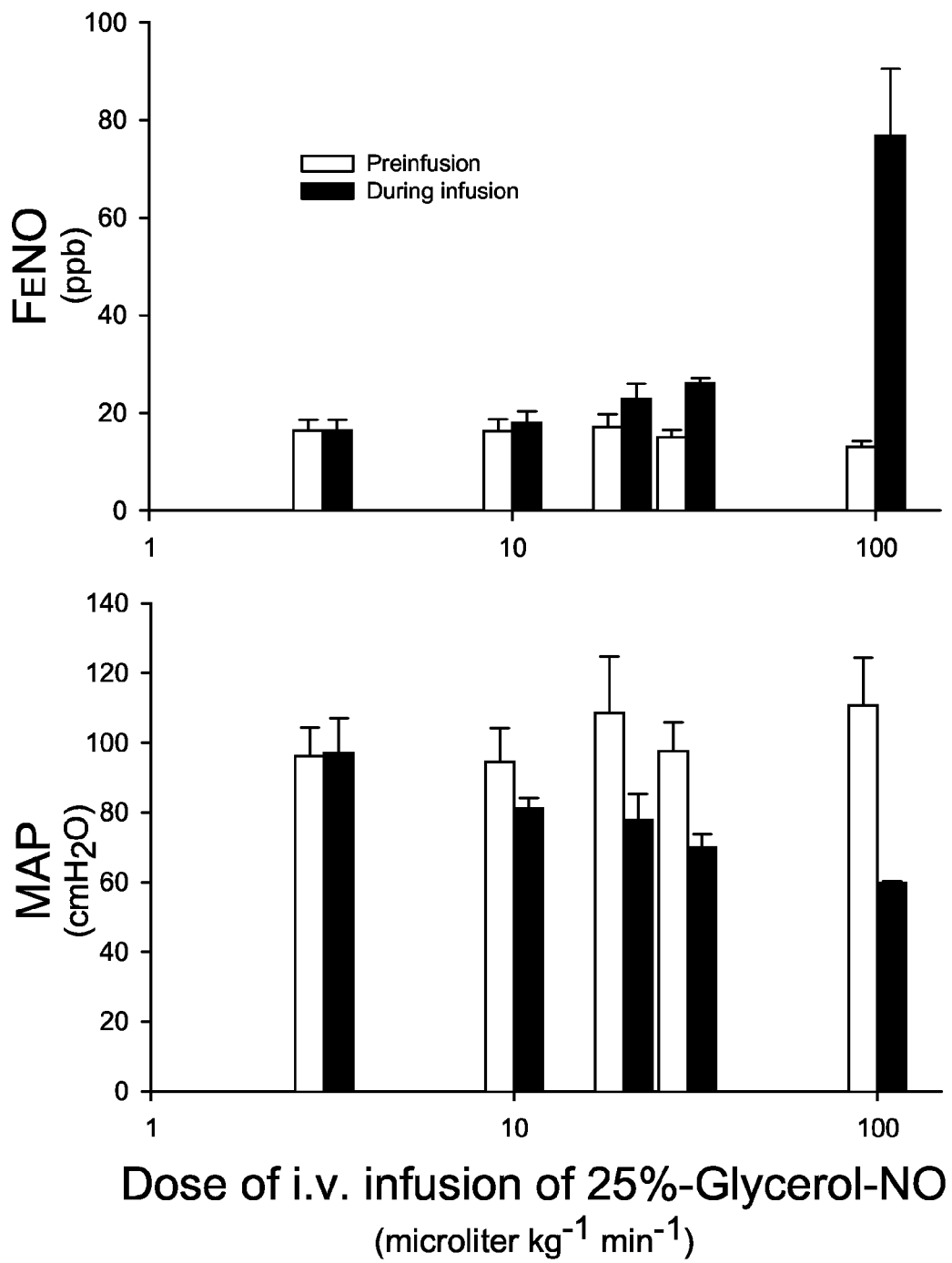

FIG. 4 consists of two diagrams relating to experiments with artificially ventilated pentobarbital anesthetized rabbits (n=3-5). The bars show mixed exhaled nitric oxide ($FENO$) and mean arterial blood pressure (MAP) before infusion (open bars) and during intravenous infusion of 25%-glycerol-NO (filled bars).

Figure 5:
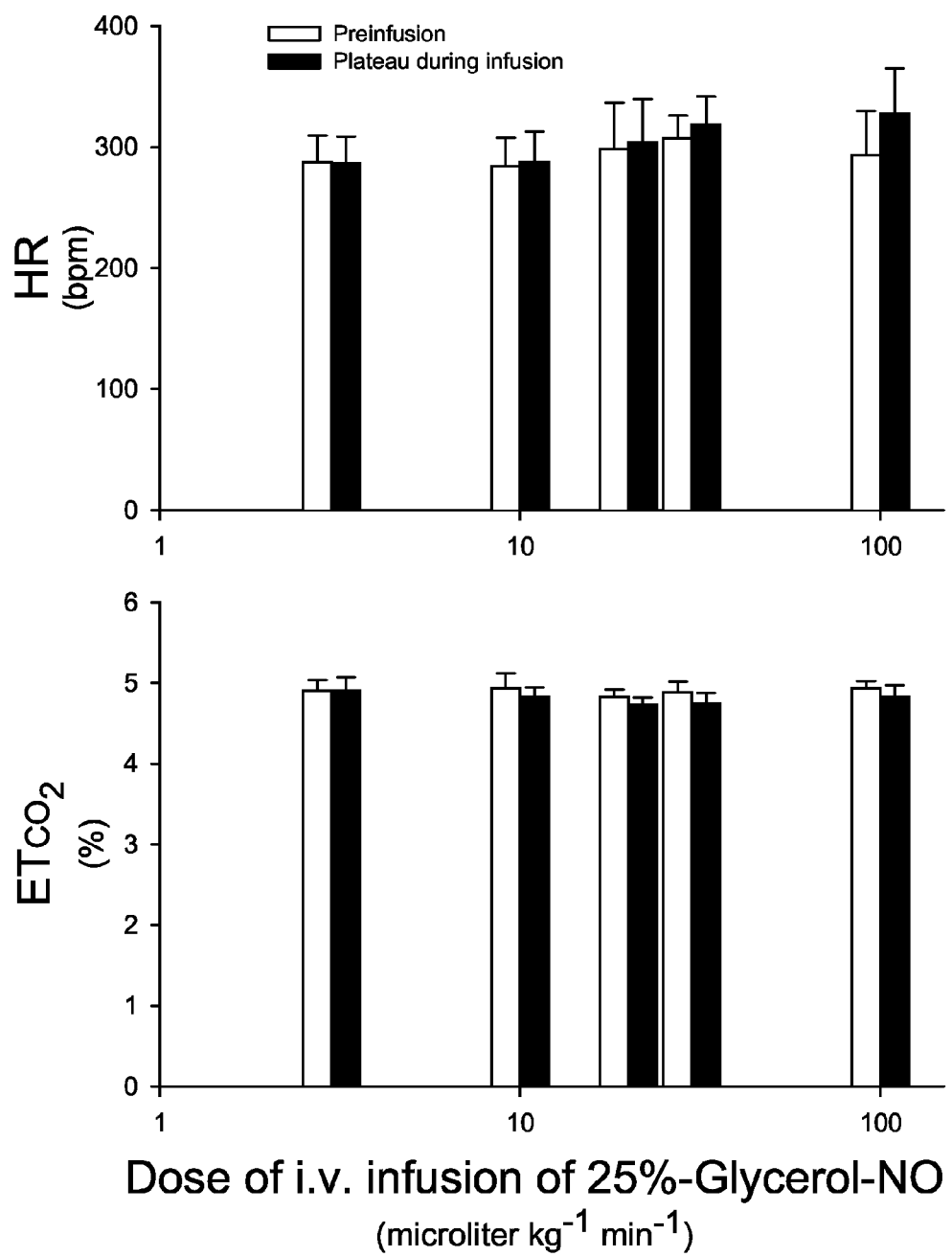

FIG. 5 consists of two diagrams relating to experiments with artificially ventilated pentobarbital anesthetized rabbits (n=3-5). The bars show heart rate (HR) and end-tidal $CO_2$ ($ET_{CO_2}$) before infusion (open bars) and during intravenous infusion of 25%-glycerol-NO (filled bars).

Figure 6:
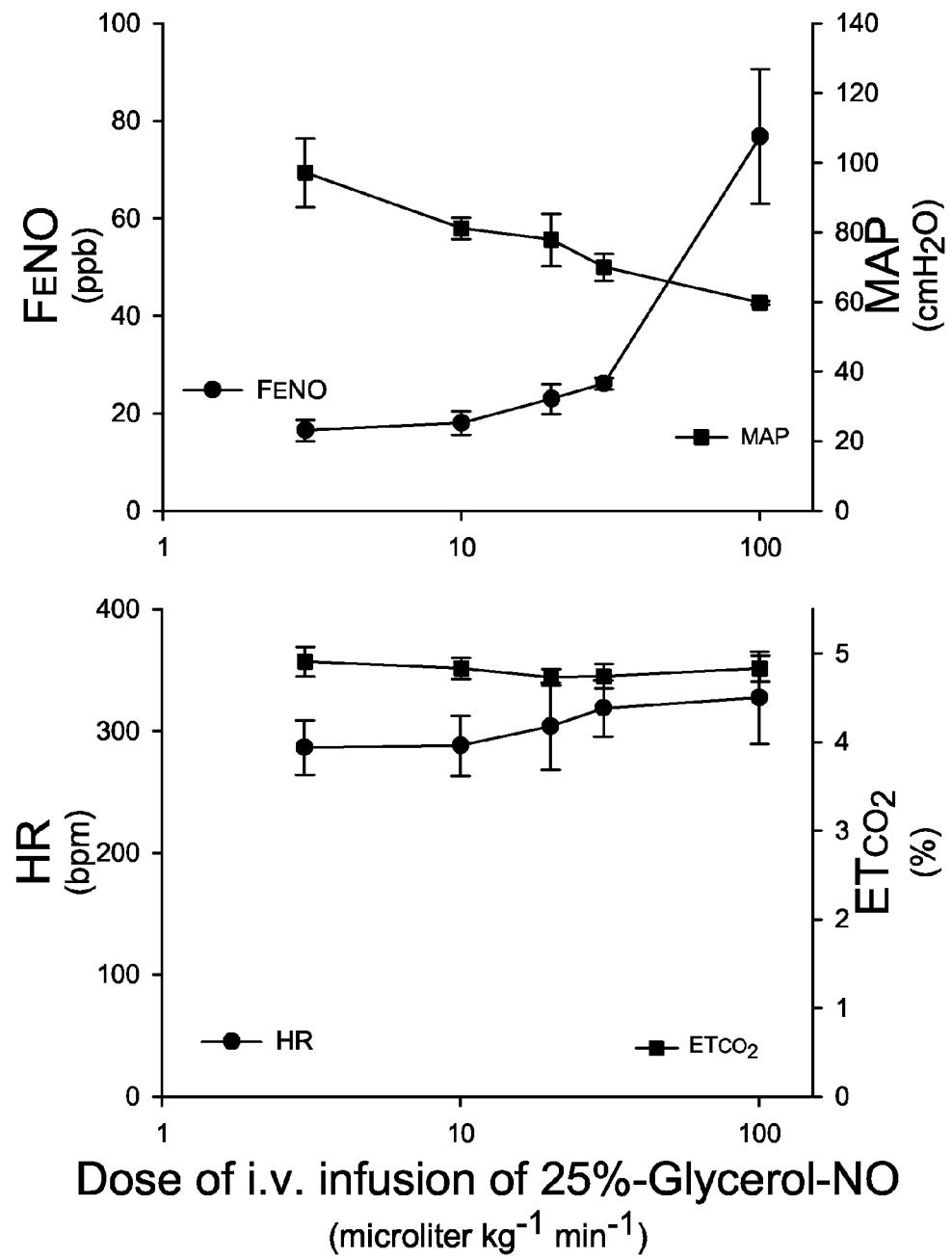

FIG. 6 consists of two diagrams relating to experiments with artificially ventilated pentobarbital anesthetized rabbits (n=3-5). The graphs show the dose and response relationships of mixed exhaled nitric oxide ($FENO$), mean arterial blood pressure (MAP), heart rate (HR) and end-tidal $CO_2$ ($ET_{CO_2}$) due to intravenous infusion of 25%-glycerol-NO.

Figure 7:
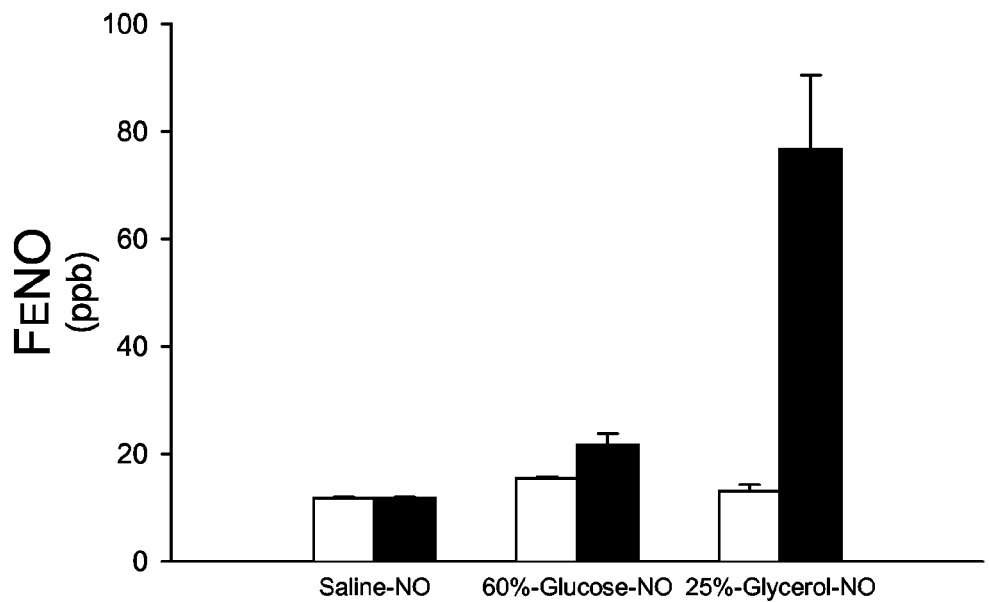
Figure 7:
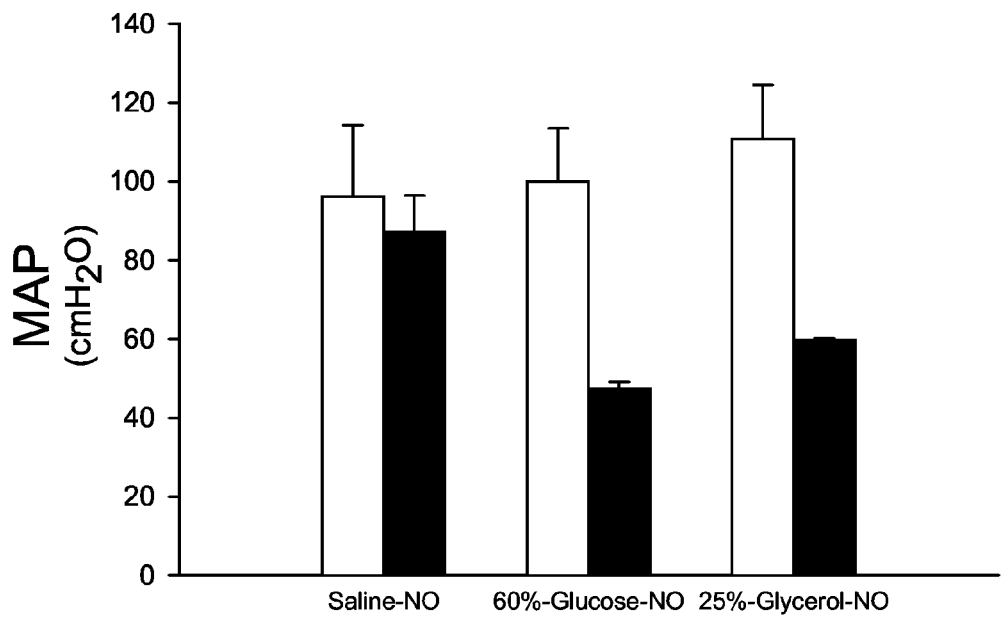

FIG. 7 consists of two diagrams relating to experiments with artificially ventilated pentobarbital anesthetized rabbits (n=2-3). The bars show mixed exhaled nitric oxide ($FENO$) and mean arterial blood pressure (MAP) before (open bars)

and during intravenous infusion of nitric oxide (NO)-substitutions to different solutions (filled bars).

Figure 8:
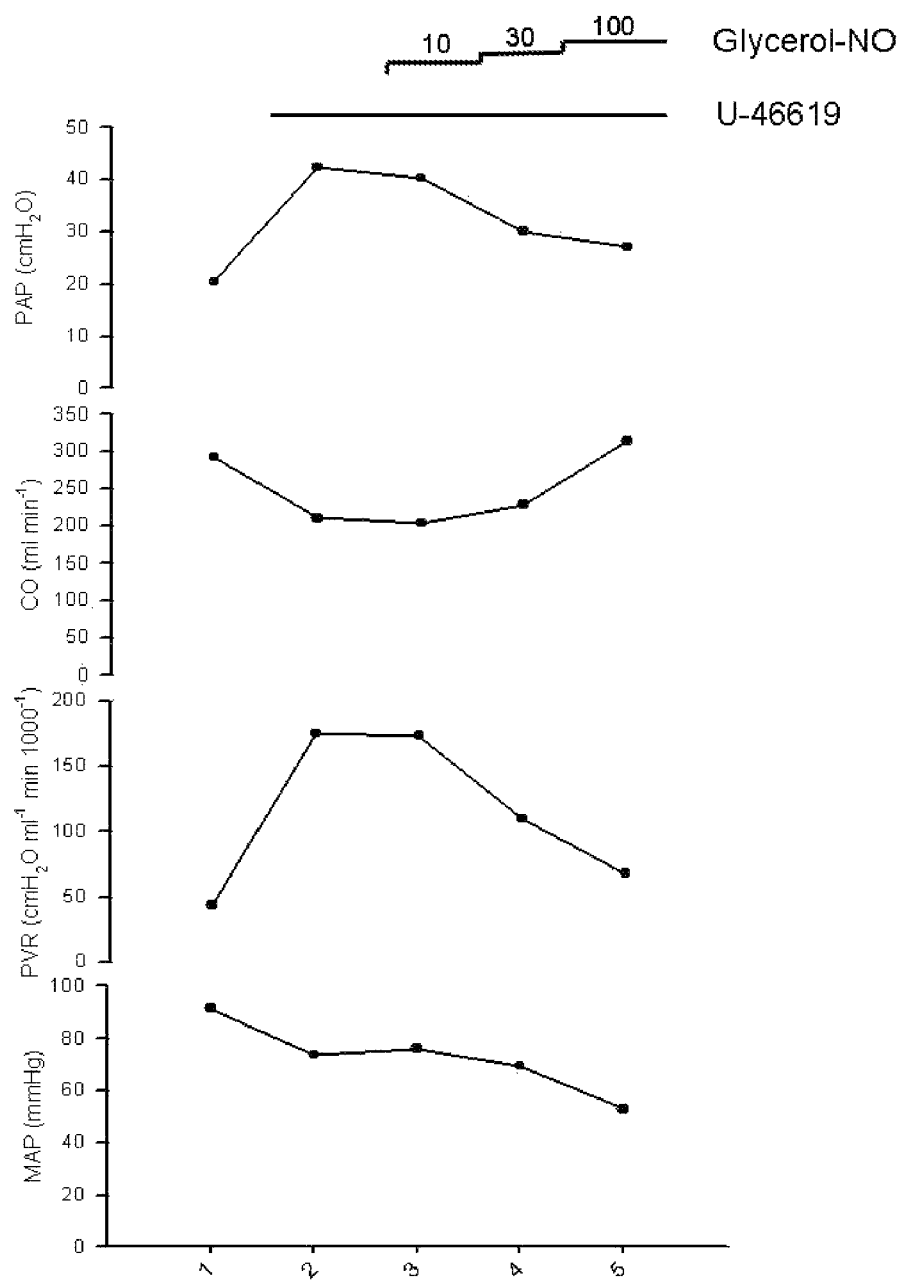

FIG. 8 shows the results from an animal experiment using a pentobarbitone-anesthetized and mechanically-ventilated rabbit. The effects of 25% glycerol-NO (doses of 10, 30 and 100 ul kg$^{-1}$ min$^{-1}$ respectively) on U46619-induced pulmonary hypertension. Abbreviations used: PAP—pulmonary artery pressure; CO—cardiac output; PVR—pulmonary vascular resistance; MAP—mean systemic arterial pressure.

Figure 9:
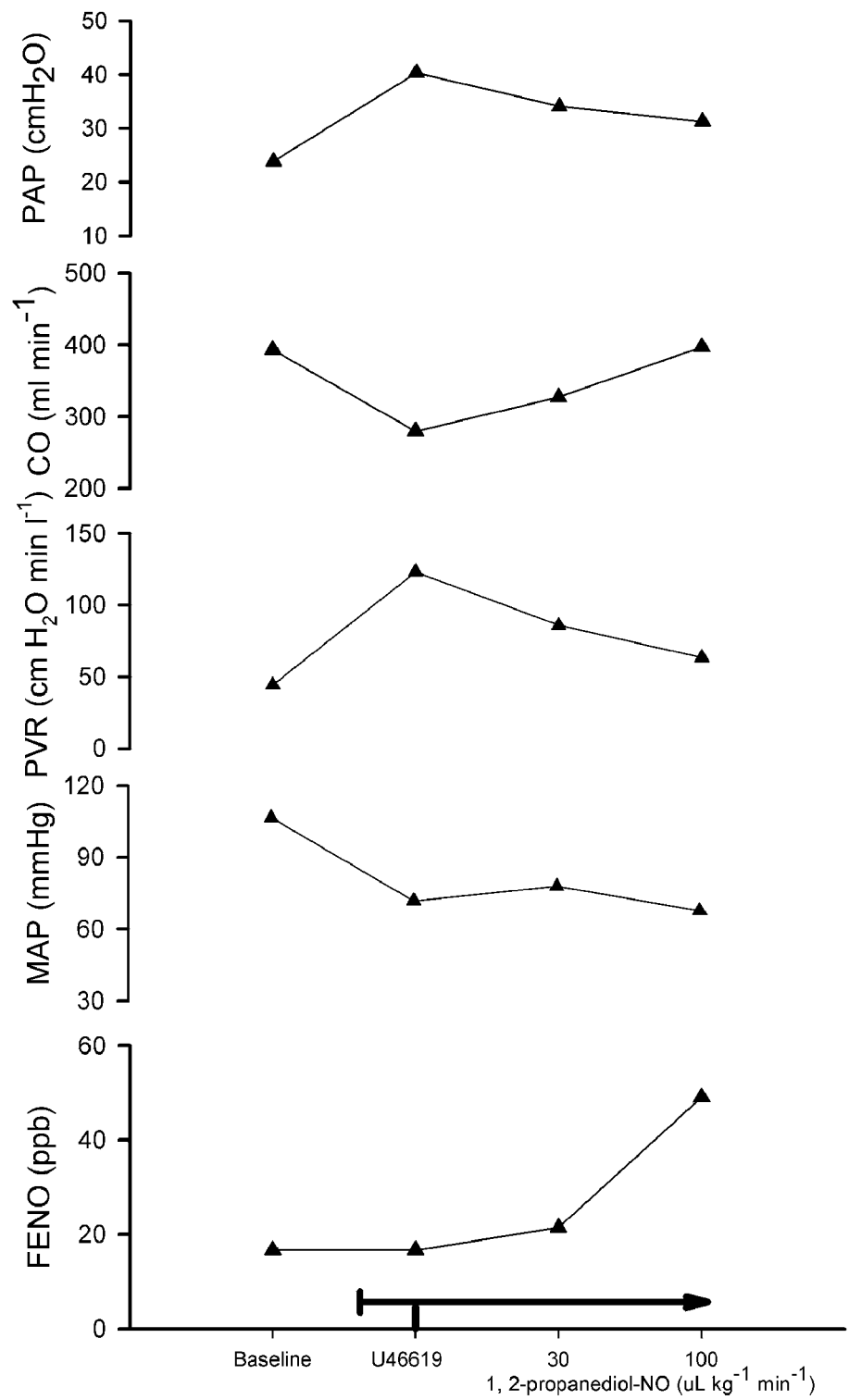

FIG. 9 shows the results from an animal experiment using a pentobarbitone-anesthetised and mechanically-ventilated rabbit. The effects of 1,2-propanediol-NO (doses of 30 and 100 μl kg$^{-1}$ min$^{-1}$ respectively) on U46619-induced pulmonary hypertension. Abbreviations used: PAP—pulmonary artery pressure; CO—cardiac output; PVR—pulmonary vascular resistance; MAP—mean systemic arterial pressure; FENO—nitric oxide concentration in mixed exhaled gas.

Figure 10:
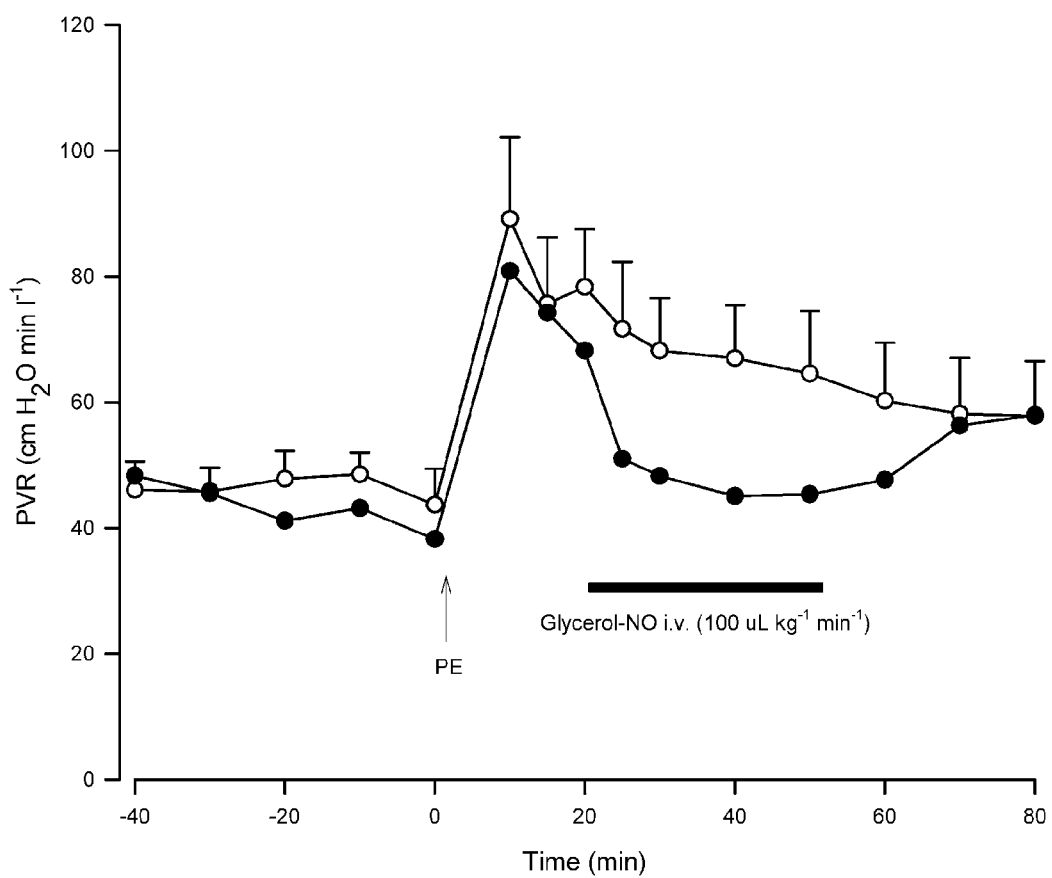

FIG. 10 shows a diagram relating to experiments where glycerol-NO was used to treat experimental pulmonary embolism (PE) in pentobarbitone-anaesthetised and mechanically ventilated rabbits. The controls (open circles, n=3) and the treated rabbit (solid circles, n=1) were given a pulmonary embolus, PE, at time 0. The treated animal received 100 μl kg$^{-1}$ min$^{-1}$ glycerol-NO i.v. (25% glycerol in water (v/v) deoxygenated and treated with pure nitric oxide gas) between the 20-50 min time points. PVR—pulmonary vascular resistance.

Figure 11:
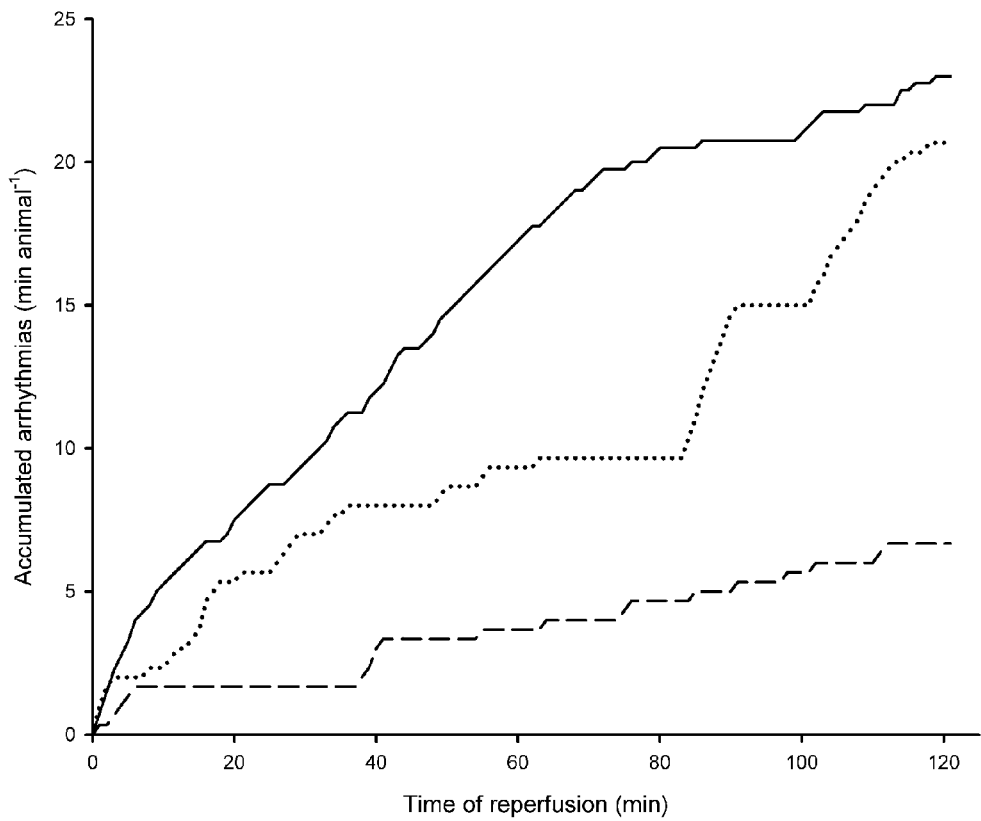

FIG. 11 shows a diagram relating to experiments on pentobarbitone-anaesthetised and mechanically ventilated rabbits where the incidence of arrhythmias during the reperfusion phase of myocardial ischemia-reperfusion injury were lowered with NO solutions i.v. The control group (solid line, n=4), the glucose-NO-treated group (dotted line, n=3), and the 1,2-propanediol-NO-treated group (long-dashed line, n=3) underwent myocardial ischemia for 30 min (not shown in the figure) and then reperfusion for 120 min (shown in the figure). The treatment started 15 min before reperfusion (i.e. after 15 min of ischemia) and was continued for 60 min of reperfusion in the glucose-NO group and for 120 min of reperfusion in the 1,2-propanediol-NO group.

Figure 12:
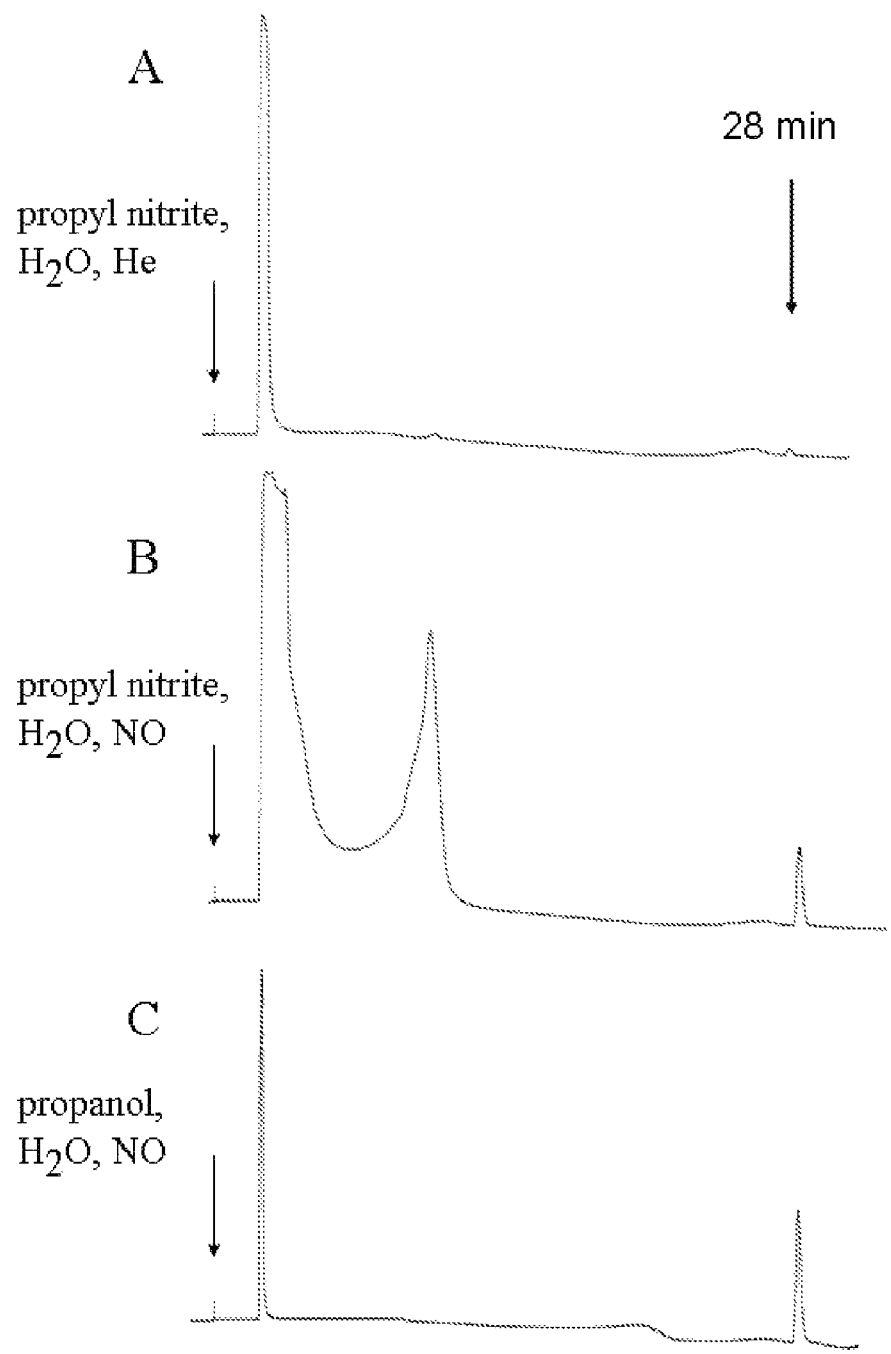

FIG. 12 shows three chromatograms from HPLC analysis of propylnitrite, propylnitrite-NO, and propanol-NO, panels A, B, and C as described in closer detail in the corresponding example.

Figure 13:
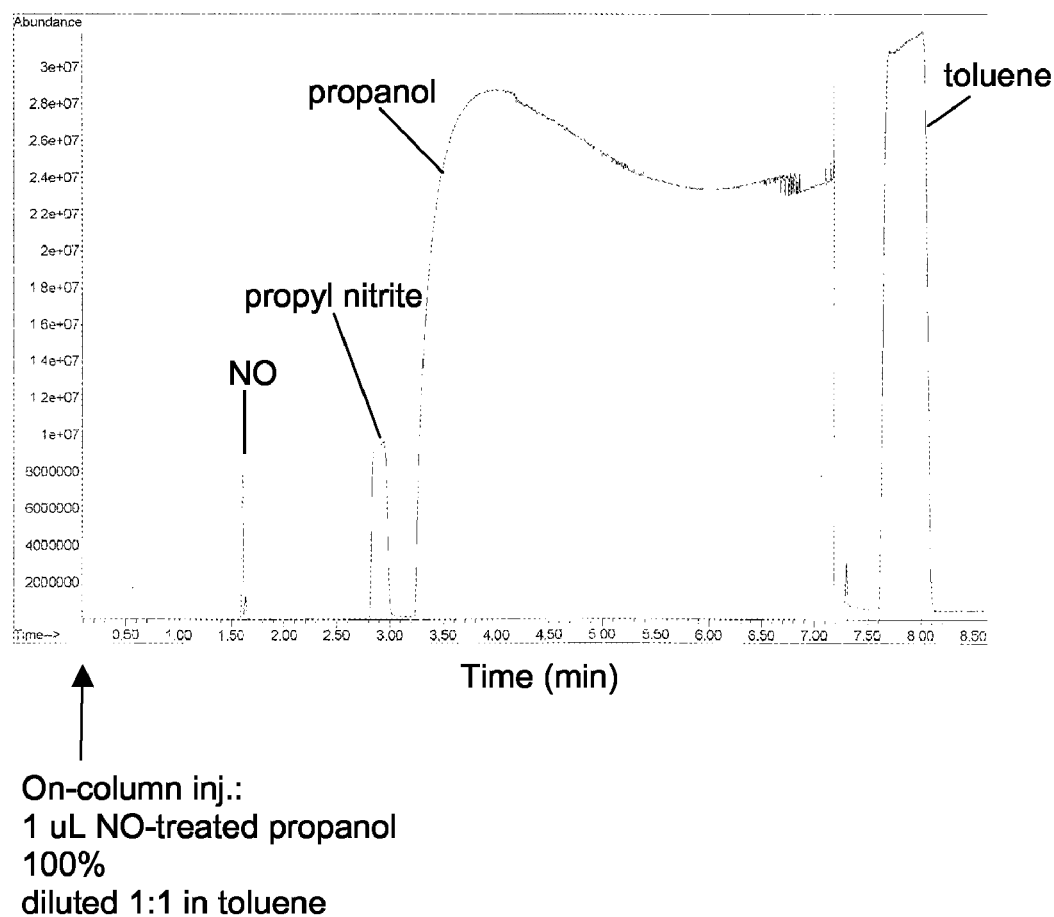

FIG. 13 shows the GC-MS analysis of a reaction between propanol (approx 100%) and NO gas under de-aerated conditions (He-purged gas-tight glass cylinder). The propanol-NO reaction mixture was sampled from the glass cylinder by a microsyringe, mixed with an equal volume of de-aerated toluene, and 1 uL of the diluted sample was injected directly on-column on an Agilent DB-5 MS 0.25 mm i.d. 30 m gas chromatography column at 40 degrees C., eluted with a constant flow of He (1 ml/min), and a temperature gradient of 10 degrees C. per min was simultaneously started. Detection was by means of a HP 5973 Mass Selective Detector (Quadrupole). Indicated compounds were detected by their respective mass spectral characteristics using a Wiley 7n mass spectral library.

Figure 14A:
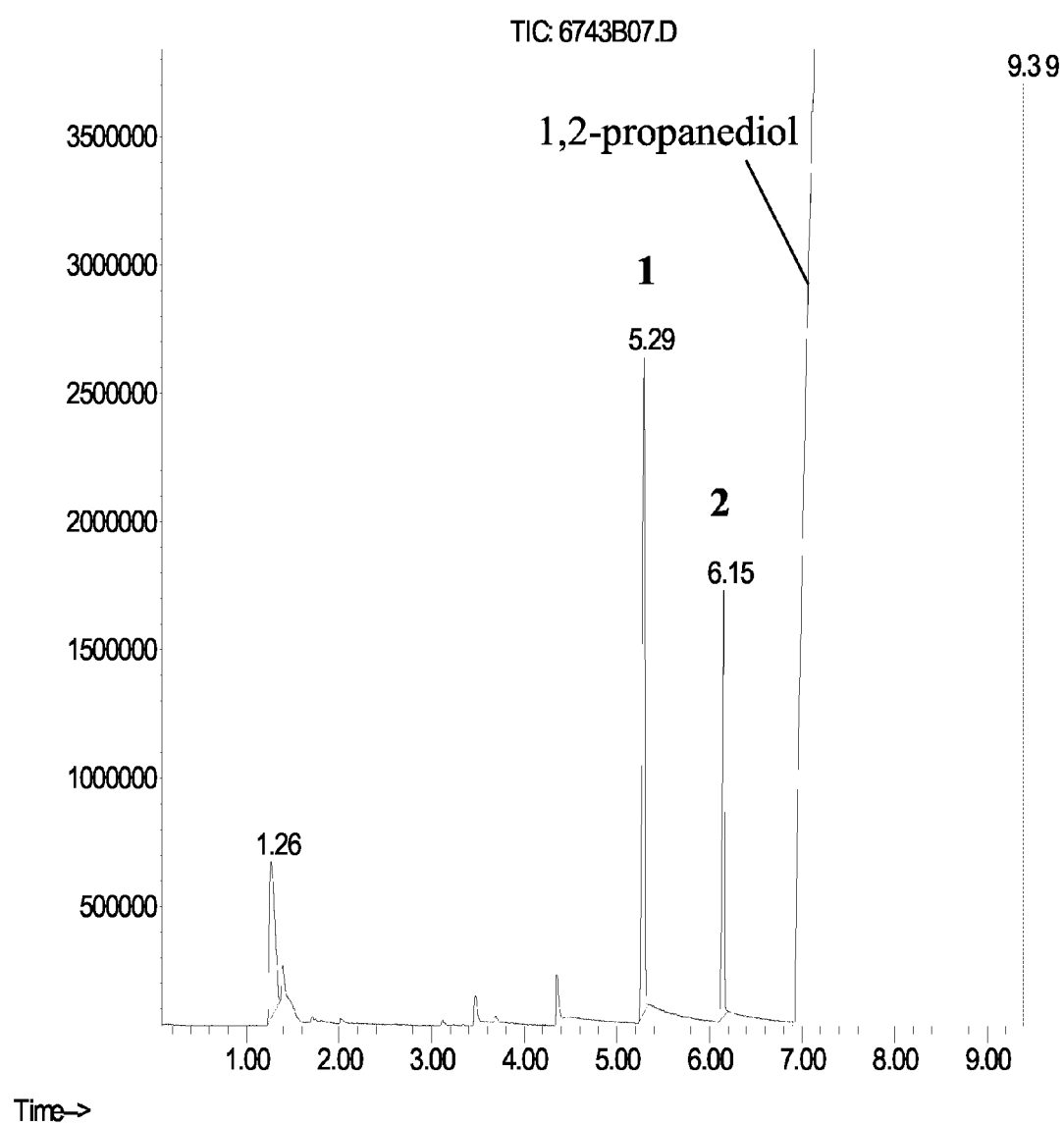
Figure 14B:
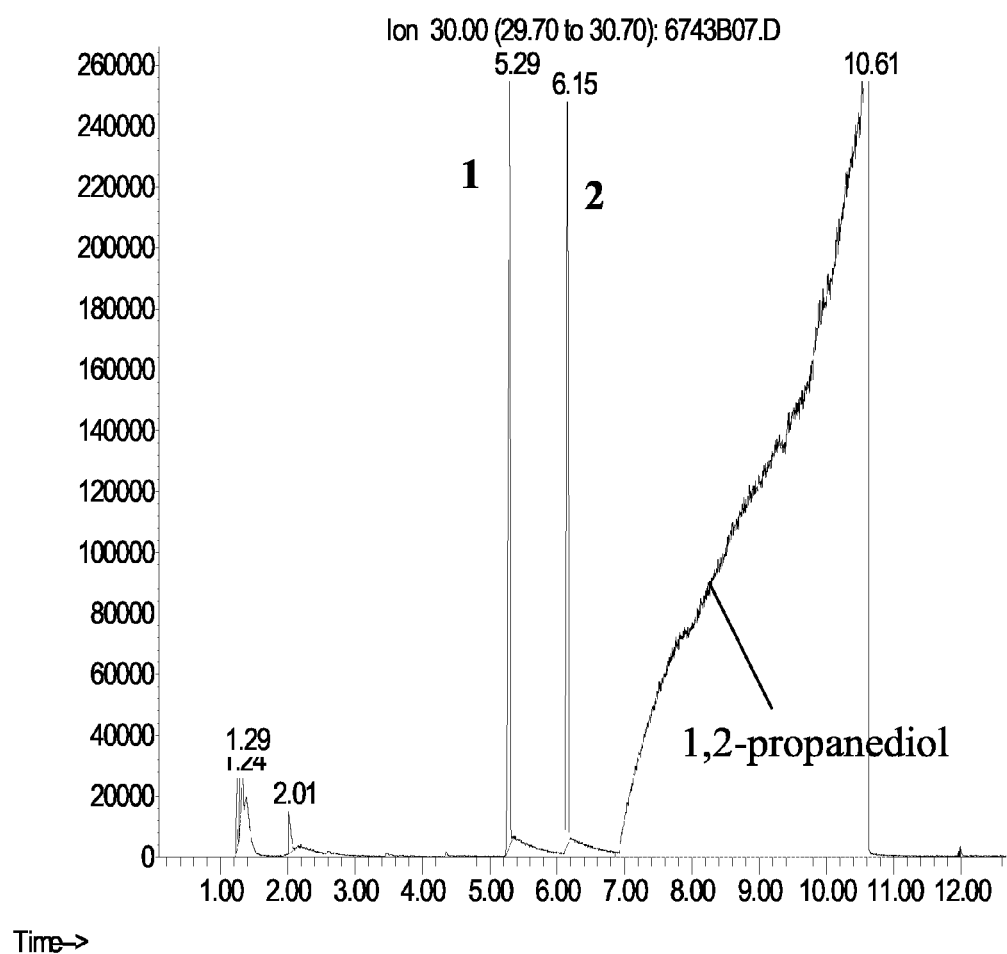

FIG. 14 shows a gas chromatogram using an Agilent DB-1701 column and with EI mass spectrometry detection after automated (split fraction 1:20) injection at time=0 of 0.5 microliter de-aerated approximately 100% 1,2-propanediol treated with NO gas. Panel A shows a total ion chromatogram for the m/z range 20-320, and panel B shows the extracted ion chromatogram for m/z=30 which is a common fragment for organic nitrites. Peaks denoted 1 and 2 are further characterized with mass spectra in FIGS. 15 and 16. The peak denoted 1,2-propanediol was identical with the corresponding entry in the Wiley mass spectral library, whereas spectra for peak 1 and 2 were not found in the Wiley library or elsewhere.

Figure 15A:
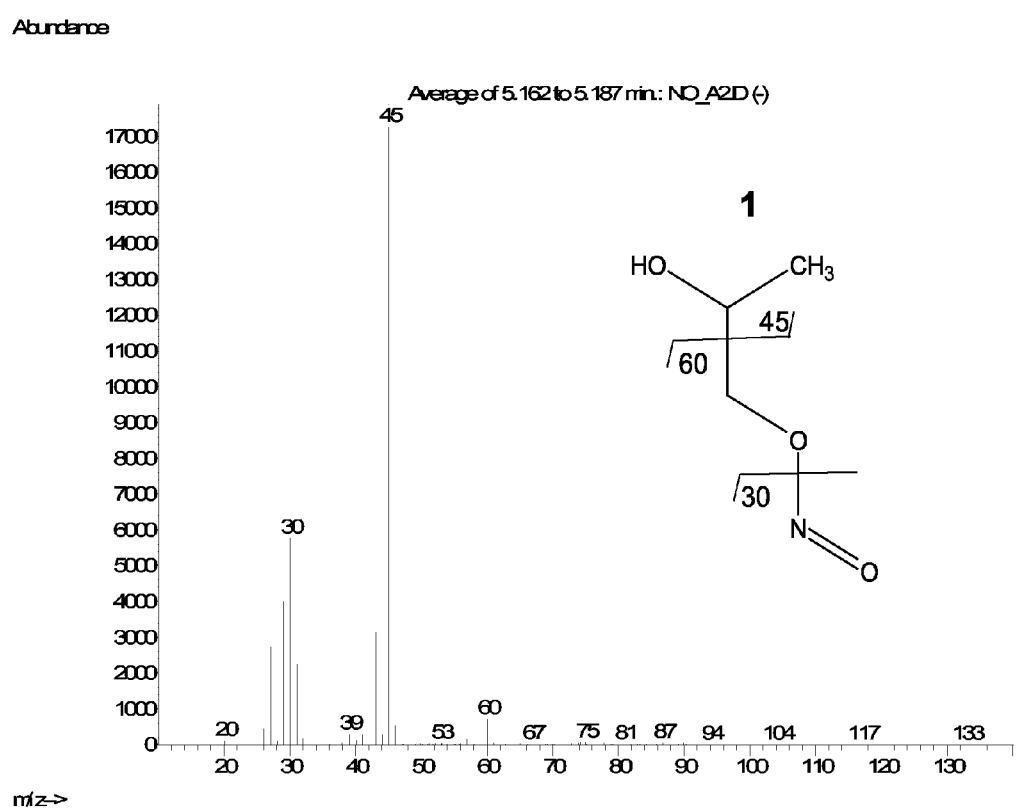
Figure 15B:
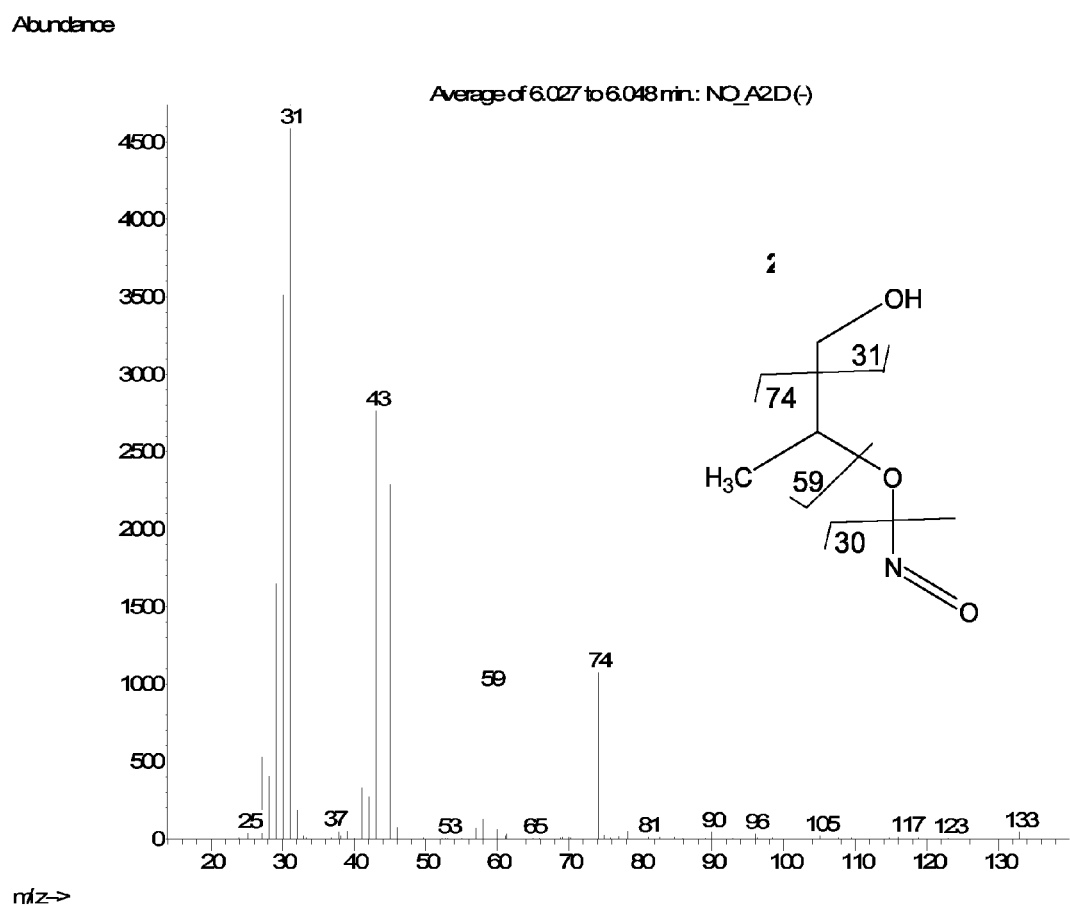

FIGS. 15a and 15b are diagrams showing EI mass spectra on peaks 1 and 2 from a similar chromatography as in FIG. 14, supporting the postulated structure of the two 1,2-propanediol nitrites (2-hydroxy propyl nitrite and 2-hydroxy-1-methylethyl nitrite) corresponding to the two peaks in FIG. 14.

Figure 16A:
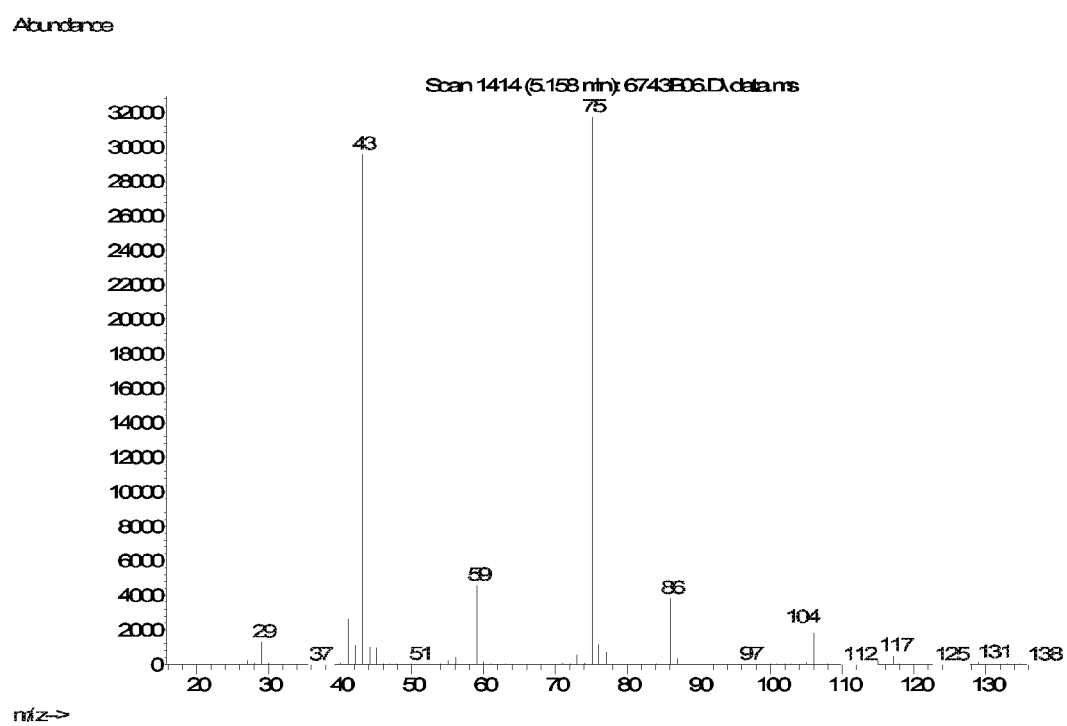
Figure 16B:
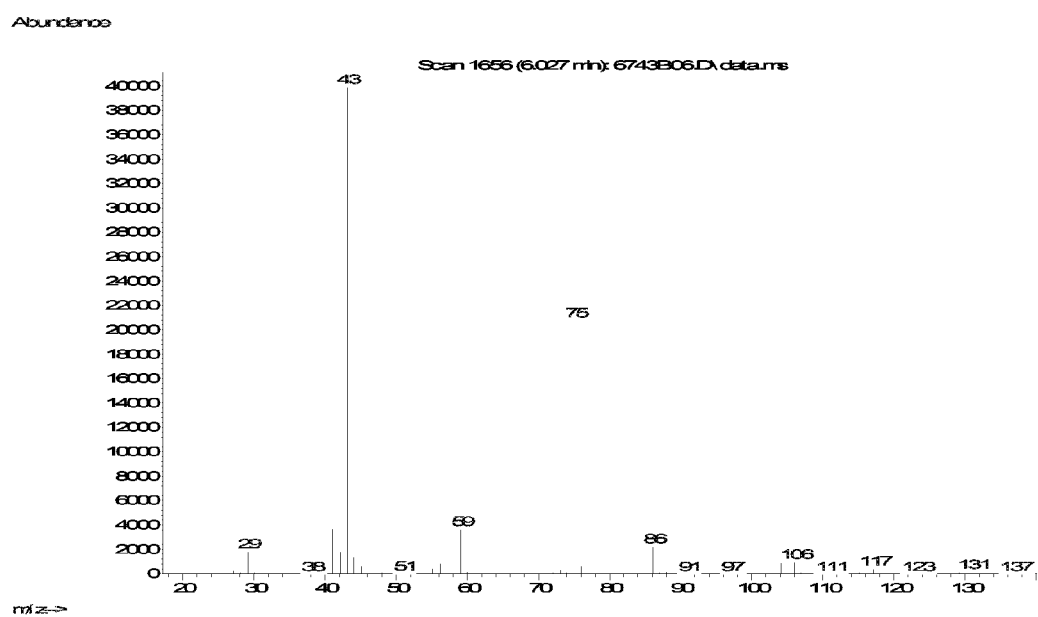

FIGS. 16a and 16b show mass spectra obtained after chromatography of the reaction mixture of de-aerated approximately 100%1,2-propanediol treated with NO gas on the Agilent DB-1701 column employing chemical ionization (methane gas). In panel A is shown the spectrum for the peak eluted corresponding to peak 1 in FIG. 14, and in panel B is shown the spectrum for the peak eluted corresponding to peak 2 in FIG. 14. In both panels are found mass peaks m/z=104 and 106, corresponding to M−1 and M+1 for the compounds described in FIG. 15.

DESCRIPTION OF EMBODIMENTS OF THE INVENTION

Before the present invention is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the claims, the singular forms "a", "an", and "the" include plural referents unless the context clearly dictates otherwise. Thus, for example, reference to an organic nitrite includes reference to one or more of such nitrites, for example a mixture of nitrites formed when performing the method according to the invention.

In initial, comparative experiments, the inventors used gaseous NO dissolved in physiological saline, given as an injection of up to 5 ml per kg body weight. Interestingly, no or only a very small increase of exhaled NO could be detected. (See FIG. 1). Similarly, no changes in blood circulation were to be seen. This indicates that NO is rapidly decomposed or otherwise inactivated when infused in saline, or that it does not reach the lungs or the systemic vessels. This is supported by the observation of significant formation of methemoglobin (See FIG. 2) during infusion of NO in saline. Methemoglobin formation is a highly undesirable effect, since it decreases the oxygen-carrying capacity of blood.

The inventors then set out to find alternative and improved compositions for the administration of gaseous NO. In this work, it was discovered that NO could be formulated as a lipid emulsion for intravenous administration, and that this formulation made it possible for the NO to reach the lungs. Experiments indicated that an infusion already of 0.1 to 0.5 ml/kg body weight results in clearly distinguishable increases in expired NO, in animals given L-NAME to inhibit the endogenous NO production. (See FIG. 1)

The results also indicate that the NO infusion exerts vasodilatory effects in the pulmonary circulation, and only mild vasodilatory effect on systemic circulation, or a combination of these effects.

A surprising observation was that very little or no methemoglobin was formed during infusion of NO in a lipid emulsion (See FIG. 2). Further experiments, using other hydroxyl containing compounds (See below) indicated a favourably low or absent formation of methemoglobin.

The inventors then tested different compounds, subjected to the method of the invention. The results are presented below, in the experimental section, and summarized in Table 1.

The compounds were produced by first de-aerating a solution consisting of or comprising the organic starting material. De-aerated here means that the starting material was rendered substantially oxygen-free. This can be achieved by purging or equilibrating the medium with an inert gas, or mixture of gases, such as nitrogen, argon, helium etc. Alternatively, the medium is passed through a gas exchange system, for example a membrane oxygenator used in reverse fashion for removal of oxygen. A distillation process, when applicable, for producing the starting material in the present invention can also be employed, when the distillation is performed under nitrogen or another inert gas or mixture of gasses to produce a de-aerated starting material for the manufacture of organic nitrites. For volatile starting materials, a de-aerated solution may also be produced by heating the starting material.

The de-aerated solution consisting of or comprising the starting material is then saturated with NO by passing gaseous NO through the starting material. This can be performed under atmospheric pressure, or under elevated pressure.

This treatment with gaseous NO presupposes that the starting material is present either in solution, or as such, in liquid or semi-solid form, making it possible to achieve satisfactory mixing with gaseous NO.

It was surprisingly found that the organic nitrites could be produced in this fashion, and that the resulting organic nitrite in many instances was of a higher purity than conventionally produced and commercially available organic nitrites. Certain organic nitrites produced here appear not to have been described before. Further, storage experiments indicate that an organic nitrite, produced according to the invention, is more stable than conventionally produced, commercial preparations. Further still, an organic nitrite produced according to the invention, is more suitable for further processing into a therapeutic formulation, e.g. dilution in a physiologically suitable vehicle.

Said vehicle is for example physiological saline, a solution or emulsion for injection or infusion. According to a preferred embodiment, said vehicle is de-aerated and saturated with gaseous NO before mixing with the organic nitrite. This makes it possible to prepare pharmaceutical formulations comprising organic nitrites without these decomposing before administration. It is believed that equilibrium conditions between the starting material, gaseous NO and the organic nitrite, stabilises the composition.

Consequently, the present invention makes available methods both for the synthesis of organic nitrites, and methods for the further processing of organic nitrites, irrespective of whether they are conventionally prepared, or synthesized according to the invention.

Compounds, suitable as the starting material for the production of an organic nitrite using the method of the invention, are preferably water miscible organic compounds, presenting at least one hydroxyl group. More preferably, said starting material is a mono/polyhydric alcohol or an aldehyde- or ketone-derivate thereof, including alcohols and mono or poly saccharides.

According to one embodiment, said starting material is a carbohydrate compound or derivates thereof. According to another embodiment, said starting material is a monosaccharide or a derivate thereof. Preferably, said starting material is chosen among glucose, fructose, galactose, ribose. For example glucose can advantageously be used in the form of commercially available carbohydrate solutions for infusion, such as but not limited to Ringer-Glucose (Baxter), glucose solutions for infusion (manufactured by Baxter, Braun, Fresenius Kabi etc.).

According to another embodiment, said starting material is a monosaccharide alcohol, preferably chosen among sorbitol and mannitol. For example mannitol can advantageously be used in the form of commercially available solutions for infusion, such as but not limited to Mannitol Baxter Viaflo® (Baxter) and Mannitol (Fresenius Kabi). In addition to functioning as a starting material, such infusion solutions can also serve as vehicles for the preparation of physiologically acceptable and therapeutically effective preparations of organic nitrites. In such embodiments of the invention, the vehicle is preferably also de-aerated and saturated with NO before addition of the organic nitrite.

According to another embodiment, said starting material is a modified monosaccharide, e.g. a compound chosen among fucose, 2-deoxy-ribose, and 1-O-methyl-ribose.

According to yet another embodiment, said starting material is a disaccharide or a higher carbohydrate polymer of a monosaccharide or derivate thereof, and preferably a disaccharide or higher polysaccharide of glucose, fructose, galactose, ribose, sorbitol, mannitol, fucose, 2-deoxy-ribose, and 1-O-methyl-ribose, or one of sucrose, lactobionic acid, inulin, dextran, and fucoidan.

Based on the positive results obtained with polymeric compounds, here exemplified by sucrose, mannitol, inulin, fucoidan, and dextran, it is apparent that the present invention is applicable to polymeric compounds. Thus, different formulations of complex carbohydrates, for example those presently used as blood substitutes and infusion solutions, can be used as starting materials and fall within the scope of the present invention. Non-limiting examples include commercially available products such as Macrodex® and Rheomacrodex® (Meda), Ringer-Dextran® (Braun), HAES-Steril, HyperHAES, and Voluvene® (Fresenius Kabi) and Hemohes® (Braun). In addition to functioning as a starting material, such products and their equivalents can also serve as vehicles for the preparation of physiologically acceptable and therapeutically effective preparations of organic nitrites. In such embodiments of the invention, the vehicle is preferably also de-aerated and saturated with NO before addition of the organic nitrite.

According to another embodiment, said starting material is an alcohol or a derivate thereof. According to this embodiment, said starting material is a monohydric alcohol, e.g. an alcohol chosen among ethanol, butanol, isobutanol, 1-propanol, 2-propanol, sorbitol, and mannitol. According to another embodiment, said starting material is a dihydric alcohol, e.g. 1,2-propanediol (propylene glycol) or 1,3-propanediol. According to yet another embodiment, said starting material is a trihydric alcohol, e.g. glycerol.

According to yet another embodiment, said starting material is a polymer of alcohol molecules or derivates thereof, e.g. polyethylene glycol of different molecular weight. Preliminary studies with PEG 400 have exhibited positive results.

Alternatively, said starting material is albumin. Thus, according to the invention, albumin based blood substitutes, such as but not limited to commercially available plasma substitutes and plasma protein infusion solutions, can be used. Examples include but are not limited to albumin infusion solutions (manufactured by Baxter, Behring, Octapharma etc.). In addition to functioning as a starting material, such albumin infusion solutions can also serve as vehicles for the preparation of physiologically acceptable and therapeutically effective preparations of organic nitrites. In such embodiments of the invention, the vehicle is preferably also de-aerated and saturated with NO before addition of the organic nitrite.

Alternatively, said starting material is a lipid emulsion, such as emulsions and solutions for intravenous nutrition, here exemplified by Intralipid®(Fresenius Kabi). Non-limiting examples of such suitable emulsions include Clinoleice® (Baxter), Omegaven®, SMOFlipid® and Structolipid® (Fresenius Kabi), and Vasolipid® (Braun) and equivalent products. In addition to functioning as a starting material, such emulsions can also serve as vehicles for the preparation of physiologically acceptable and therapeutically effective preparations of organic nitrites. In such embodiments of the invention, the vehicle is preferably also de-aerated and saturated with NO before addition of the organic nitrite.

The invention makes available compounds, prepared using the inventive method, as well as compositions containing such compounds. Examples of such compounds, presently believed to be novel, include two novel NO-donors having the formulas I and II below:

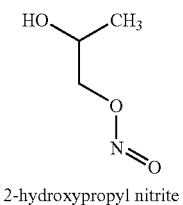

2-hydroxypropyl nitrite

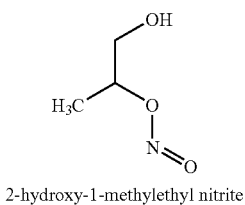

2-hydroxy-1-methylethyl nitrite

The structure of the above compounds is confirmed by mass spectrometry analysis, as described in closer detail in the experimental section of the description.

These, and other compounds prepared using the inventive method can be used either as such, or as part of a pharmaceutical composition.

The composition is optionally produced or prepared for storage using a method according to the invention.

The composition according to the invention is preferably formulated for topical, rectal, vaginal, intrauterine, intraurethral, intrarectal, intravesical, intra- or transcervical, intrauterine, laparoscopic, intrasurgical, nasal, ocular, sublingual, buccal, oral, enteral, intravenous, intraarterial, intratracheal, intramuscular or subcutaneous administration, as well as administration via inhalation.

According to a preferred embodiment, the composition according to the invention contains substantially no oxygen. Further, according to another preferred embodiment, said composition is an injectable aqueous formulation containing an organic nitrite substantially in the absence of oxygen. For stability purposes, it is further contemplated that the composition is stored in an environment saturated with gaseous NO, for example in an environment saturated with NO, or in the presence of an excess of gaseous NO or under a headspace of NO. Preliminary results indicate that an organic nitrite is more stable against decomposition and the formation of unwanted reaction product if the organic nitrite, the corresponding organic starting material, and gaseous NO are simultaneously present.

One preferred embodiment is an aqueous formulation for inhalation, comprising an organic nitrite, and suitable for administration using conventional techniques such as nebulization, aerosolization etc. Preferably said formulation comprises the organic nitrite, the corresponding organic starting material and gaseous NO.

Another preferred embodiment is a formulation for topical administration, such as a gel, ointment or solution, comprising an organic nitrite, the corresponding organic starting material and gaseous NO.

Another preferred embodiment is a formulation for infusion, such as a sterile solution or emulsion, comprising an organic nitrite, the corresponding organic starting material and gaseous NO.

Further, the present invention makes available a method for the treatment, alleviation or prevention of insufficient perfusion in an organ or organs in a human or animal patient, wherein a composition, capable of delivering NO is given to said patient. Insufficient perfusion includes states of insufficient perfusion of various etiology, in tissues or organs, including but not limited to ischemic tumor tissue, transplanted tissues or organs, including organs or tissues intended for transplantation.

According to one embodiment of the invention, said insufficient perfusion is insufficient perfusion of a section or sections of a lung, due to pulmonary embolism. Pulmonary embolism includes pulmonary embolism of various etiology, including but not limited to pulmonary thromboembolism and pulmonary gas embolism.

Other indications, where the inventive composition is used either alone, or in combination with one or more pharmaceutical agents, include acute pulmonary vasoconstriction of different genesis, pulmonary embolism, pulmonary hypertension of different genesis, including primary hypertension and secondary hypertension, systemic hypertension of different genesis, acute heart failure, coronary heart disease, myocardial infarction, ischemic heart disease, angina pectoris, instable angina, cardiac arrhythmia, acidosis, inflammation of the airways, cystic fibrosis, COPD, immotile cilia syndrome, inflammation of the lung, pulmonary fibrosis, adult respiratory distress syndrome, acute pulmonary edema, acute mountain sickness, asthma, bronchitis, hypoxia of different genesis, stroke, inflammation of the gastrointestinal tract, IBD, Crohn's disease, ulcerous colitis, inflammation of the bladder or the urethral tract, inflammation of the skin, diabetic ulcers, diabetic neuropathy, psoriasis, inflammation of different genesis, wound healing, and conditions where smooth muscle relaxation is needed.

According to a preferred embodiment, the indication is asthma, and the inventive composition is formulated as a preparation for inhalation.

The composition may also be used in situations where controlled hypotension is desired, e.g. controlled hypotension during neurosurgery.

The inventive composition is also preferably used alone, or in combination with one or more pharmaceutical agents, to act as an inhibitor of trombocyte aggregation and coagulation, e.g. in combination with vasodilatation.

The inventive composition is also used as an adjunct to other pharmaceutically active agents, in order to increase their uptake, e.g. to increase the systemic uptake of topically administered systemic drugs; as an addition to injections, where increased local circulation is desired; as an adjunct to anti-tumour drugs and/or in conjunction with irradiation therapy, where a vasodilatory effect may increase the anti-tumour effects of the treatment. Another application is wound healing, where the combined delivery of an antimicrobial agent, an antibiotic or the like, and an organic nitrite is contemplated.

According to an embodiment of this use, said insufficient perfusion in an organ or organs is insufficient perfusion of a section or sections of a lung, due to pulmonary embolism. Pulmonary embolism includes pulmonary embolism of various etiology, including but not limited to pulmonary thromboembolism and pulmonary gas embolism. Pulmonary hypertension, e.g. of the newborn, or primary or idiopathic pulmonary hypertension or pulmonary hypertension secondary to another disease or hypoxia can also be treated by means of the invention.

Thus, the present invention also makes available first and second medical uses of the organic nitrites produced according to the invention, as well as organic nitrite containing formulations, prepared according to the invention. In general terms, the invention makes available the use of an organic nitrite, or a composition comprising an organic nitrite, for the manufacture of a pharmaceutical formulation for the treatment of a condition where the formation of NO has beneficial effect.

In the above first or second medical use, said organic nitrite is an organic nitrite formed when subjecting an organic starting material to the method of the invention, wherein said starting material is chosen among glucose, fructose, galactose, ribose, sorbitol, mannitol, fucose, 2-deoxy-ribose, 1-O-methyl-ribose, sucrose, lactobionic acid, inulin, dextran, fucoidan, ethanol, butanol, isobutanol, 1-propanol, 2-propanol, 1,2-propanediol (propylene glycol), 1,3-propanediol, glycerol, polyethylene glycol, N-acetyl-cysteine, albumin, and derivatives thereof.

According to the invention, said condition is chosen among acute pulmonary vasoconstriction of different genesis, pulmonary embolism, pulmonary hypertension of different genesis, including primary hypertension and secondary hypertension, systemic hypertension of different genesis, acute heart failure, coronary heart disease, myocardial infarction, ischemic heart disease, angina pectoris, instable angina, cardiac arrhythmia, acidosis, inflammation of the airways, cystic fibrosis; COPD, immotile cilia syndrome, inflammation of the lung, pulmonary fibrosis, adult respiratory distress syndrome, acute pulmonary edema, acute mountain sickness, asthma, bronchitis, hypoxia of different genesis, stroke, inflammation of the gastrointestinal tract, IBD, Crohn's disease, ulcerous colitis, inflammation of the bladder or the urethral tract, inflammation of the skin, diabetic ulcers, diabetic neuropathy, psoriasis, inflammation of different genesis, wound healing, and conditions where smooth muscle relaxation is needed.

In the above, a pharmaceutical formulation is one of a plaster or bandage, a gel, a cream, an ointment, a solution, a suppository for topical, rectal or vaginal administration; a solution, for drop-wise addition or for forming an aerosol for nasal or ocular administration; a solution, emulsion, drops, capsules or tablets for oral or enteral administration; an injectable solution or emulsion for intravenous, intra-arterial, intratracheal, intramuscular or subcutaneous administration, or a solution for inhalation.

The present invention also makes available a method for the manufacture of an organic nitrite, wherein a aqueous solution, suitable for topical, rectal, vaginal, intraurethral, intravesical, intrarectal, nasal, ocular, sublingual, buccal, oral, enteral, intravenous, intra-arterial, intratracheal, intramuscular or subcutaneous administration, or administration via inhalation, is de-aerated until substantially free from oxygen, and then purged with pure NO gas until a desired NO concentration is reached.

In the method according to the invention, said starting material for producing the organic nitrite is preferably a water miscible organic compound, presenting at least one hydroxyl group. Preferably said starting material is a mono/polyhydric alcohol or an aldehyde- or ketone-derivative thereof.

According to one embodiment, said starting material is a carbohydrate compound or a derivative thereof. According to another embodiment, said starting material is a monosaccharide or a derivate thereof. Preferably, said starting material is chosen among glucose, fructose, galactose, ribose.

According to another embodiment, said starting material is a monosaccharide alcohol, preferably chosen among sorbitol and mannitol.

According to another embodiment, said starting material is a modified monosaccharide, e.g. a compound chosen among fucose, 2-deoxy-ribose, and 1-O-methyl-ribose.

According to yet another embodiment, said starting material is a disaccharide or a higher carbohydrate polymer of a monosaccharide or derivate thereof, and preferably a disaccharide or higher polysaccharide of glucose, fructose, galactose, ribose, sorbitol, mannitol, fucose, 2-deoxy-ribose, and 1-O-methyl-ribose, or one of sucrose, lactobionic acid, inulin, dextran, and fucoidan.

As noted above, based on the positive results obtained with polymeric carbohydrates, here exemplified by sucrose, mannitol, inulin, fucoidan, and dextran, it is apparent that different formulations of complex carbohydrates, presently used as blood substituents and infusion solutions, fall within the scope of the present invention. Non-limiting examples include Macrodex® and Rheomacrodex® (Meda), Ringer-Dextran® (Braun), HAES-Steril, HyperHAES, and Voluven® (Fresenius Kabi) and Hemohes® (Braun).

According to another embodiment, said starting material is an alcohol or a derivate thereof. According to this embodiment, said starting material is a monohydric alcohol, e.g. an alcohol chosen among ethanol, butanol, isobutanol, 1-propanol, 2-propanol, sorbitol, and mannitol. According to another embodiment, said starting material is a dihydric alcohol, e.g. 1,2-propanediol (propylene glycol) or 1,3-propanediol. According to yet another embodiment, said starting material is a trihydric alcohol, e.g. glycerol.

According to yet another embodiment, said starting material is a polymer of alcohol molecules or derivates thereof, e.g. polyethylene glycol of different molecular weight. Preliminary studies with PEG 400 have exhibited positive results.

Alternatively, said starting material is albumin. Thus, according to the invention, albumin based blood substituents, such as but not limited to commercially available plasma substitutes and plasma protein infusion solutions, can be used. Non-limiting examples include albumin infusion solutions (manufactured by Baxter, Behring, Octapharma etc.).

Alernatively, said composition is a lipid emulsion, such as emulsions and solutions for intravenous nutrition, here exemplified by Intralipid® (Fresenius Kabi). Non-limiting examples of such suitable emulsions include Clinoleic® (Baxter), Omegaven®, SMOFlipid® and Structolipid® (Fresenius Kabi), and Vasolipid® (Braun) and equivalent products.

The present invention also makes available a NO-saturated, substantially oxygen-free and physiologically acceptable composition, obtainable by a method as described above.

The composition according to the invention is preferably formulated as a plaster or bandage, a gel, a cream, an ointment, a solution, a suppository for topical, rectal, vaginal, intraurethral, intrarectal or intravesical administration. It is preferably formulated as a solution, for drop wise addition or for forming an aerosol for nasal or ocular administration. It is preferably formulated as a solution, emulsion, drops, capsules or tablets for oral or enteral administration. It is preferably formulated as an injectable solution or emulsion for intravenous, intra-arterial, intratracheal, intrarectal, intramuscular or subcutaneous administration, or a formulation for inhalation.

When preparing the organic nitrite or a formulation comprising an organic nitrite according to the present invention, it is important that the starting material and/or reaction medium is/are de-aerated before addition of NO. The term "de-aerated" here means that the starting material is rendered substantially oxygen-free. This can be achieved by purging or equilibrating the medium with an inert gas, or mixture of gases, such as nitrogen, argon, helium etc. Alternatively, the medium is passed through a gas exchange system, for example a membrane oxygenator used in reverse fashion for removal of oxygen. A distillation process, when applicable, for producing the starting material in the present invention can also be employed, when the distillation is performed under nitrogen or another inert gas or mixture of gasses to produce a de-aerated starting material for the manufacture of organic nitrites. For volatile starting materials, a de-aerated solution may also be produced by heating the starting material.

According to a preferred embodiment, the organic nitrite is stored in an environment saturated with NO, or under a headspace of NO.

In practice, the storage vessels, vials, syringes, bottles or bags, as well as the tubes and cannulas should be non-permeable to oxygen or at least have reduced permeability to oxygen. A skilled person can easily identify suitable packaging materials. Except for this consideration, conventional apparatuses and practises for administering pharmaceuticals can be used.

Advantages

One important clinical advantage of the present invention is that the effects of the organic nitrite, when administered to the patient in a composition according to the invention, will be most significant in hypoxic tissue. When the NO forming compound is given as an intravenous infusion, the risk of so called proximal steal, i.e. increased blood flow in neighbouring healthy vessels, is avoided. This is a common side effect of vasodilating substances, leading to lowered blood pressure and related systemic symptoms.

Another advantage is that the manufacture of the organic nitrites is easy, repeatable and requires no harsh conditions, which may alter or damage other components optionally present in the composition.

Another advantage is that the organic nitrites produced according to the invention, appear to be more stable, and are better suited for mixing with physiological carriers or vehicles.

Yet another advantage is that the release of NO seems to be non-enzymatic, based on an experiment using a perfused lung model. A non-enzymatic release mechanism indicates that a composition according to the invention would avoid the tolerance development, associated with conventional NO-donating compositions.

Yet another advantage, especially in comparison with administration of NO in saline only, or NO in carbon dioxide, is the considerably lower formation of methemoglobin.

Further advantages will become evident to a skilled person upon study of the description and examples.

EXAMPLES

1. Intravenous Infusion of NO Dissolved in Liquid Medium

Experiments were approved by the local ethics committee on animal experimentation. A male New Zealand white rabbit was anesthetised, prepared and examined as in the protocol presented in Example 2. The rabbit was pre-treated with L-NAME (30 mg $kg^{-1}$) and received one infusion with NO-gas dissolved in normal saline and one with NO-gas dissolved in lipid emulsion (INTRALIPID®, Fresenius Kabi) through the catheter in the jugular vein without carrier flow. The infusion rate was for both liquids 0.5 ml $kg^{-1}$ $min^{-1}$. There was a recovery period between the two infusions for about 200 min.

The infusion liquids were created the same way. First the liquid was de-aerated for 20 min, in a gas-tight glass chamber with a rubber membrane with an inert gas; in this case helium gas, but nitrogen, argon etc could also be used. After this no oxygen were allowed to enter the liquid throughout the following procedure. The liquid was then purged with pure NO of a few minutes. The liquid was then collected through the rubber membrane in a gas-tight syringe with needle and from this syringe infused by means of syringe pump (864 Syringe Pump, Univentor LTD., Zejtun, Malta) in the jugular vein catheter.

Drugs

Heparin was purchased from Kabi Vitrum, Stcokholm, Sweden, pancuronium bromide (PAVULON®) was from Organon, Oss, Holland, sodium pentobarbital was from Apoteksbolaget, Stockholm, Sweden and dextran 70 (MACRODEX®) was from Pharmalink, Spånga, Sweden. L-NAME ($N^G$-nitro-L-arginine methyl ester) and routine chemicals were purchased from Sigma Chemical Company, St Louis, Mo., USA.

Effects of L-NAME-Infusion

Infusion of L-NAME (30 mg $kg^{-1}$) throughout 10 min decreased exhaled nitric oxide (from 19 ppb to <1 ppb, FIG. 1), increased systemic mean arterial blood pressure (MAP, from 103 $cmH_2O$ to 128 $cmH_2O$ (Data not shown in figure)), and lowered heart rate (HR, from 274 beats $min^{-1}$ to 258 beats $min^{-1}$ (Data not shown in figure)). End-tidal $CO_2$ and the relevant blood gas parameters were normal.

Infusion of NO-gas Dissolved in Normal Saline

Rapid infusion (0.5 ml $kg^{-1}$ $min^{-1}$ during 30 min) of NO-gas dissolved in normal saline decreased MAP (from 128 $cmH_2O$ to 75 $cmH_2O$ (Data not shown in figure)), increased HR (from 258 beats $min^{-1}$ to 295 beats $min^{-1}$ (Data not shown in figure)), and slightly increased exhaled nitric oxide (from 0 ppb to 2.5 ppb, FIG. 1). The methemoglobin (metHb) fraction increased dramatically (from 0.1% to 20%, FIG. 2). About 200 min after the infusion, the animal had almost completely recovered, and exhaled NO, MAP, HR and metHb were 0.8 ppb, 123 $cmH_2O$, 313 beats $min^{-1}$ and 2.5% respectively.

Infusion of NO-gas Dissolved in Lipid Emulsion

Upon infusion (0.5 ml $kg^{-1}$ $min^{-1}$ during 30 min) of NO-gas dissolved in lipid emulsion exhaled NO increased (from 0.8 ppb to 32.5 ppb, FIG. 1), MAP fell from 106 $cmH_2O$ to 55 $cmH_2O$ while HR and metHb fraction (FIG. 2) were hardly affected.

Discussion on Intravenous Infusion of NO Dissolved in Liquid Medium

The results clearly show that the administration of NO, via the blood circulation to the lungs, dissolved in a liquid medium, is heavily increased (about 15 times), monitored as exhaled NO, when NO is dissolved in lipid emulsion compared to normal saline. The present inventors point out a noticeable disadvantage of dissolving NO in normal saline compared to lipid emulsion, in that metHb is greatly increased. Generation of metHb may be serious if arterial oxygen saturation is reduced, for example in conditions with pulmonary hypertension such as pulmonary embolism. In this experiment, the present inventors used a very high infusion rate and therefore MAP decreased significantly, but believe that a much slower infusion rate is sufficient to generate beneficial effects in the lung in conditions with pulmonary hypertension or thromboembolism and may achieve this without causing a major decrease in the systemic arterial blood pressure. Notice that exhaled NO increased to 32.5 ppb from <1 ppb and that normal levels of NO in mixed exhaled breath is approximately 20 ppb. Further it might not be necessary to generate these levels in exhaled gas as the beneficial effects probably are on the vasculature. The magnitude of the fall in MAP could also partly be due to the inhibition of endogenous NO generation.

In another experiment, the present inventors successfully treated venous gas embolism with NO dissolved in lipid emulsion, in an animal with inhibited NO production, whereas it was impossible to treat the same with inhaled nitric oxide in the same experimental setting. The beneficial effects may be induction of vasodilation in the pulmonary vasculature, inhibition of aggregation of trombocytes and/or minor vasodilation in the whole or parts of the systemic circulation, for example in the coronary circulation.

2. Animal Studies for the Evaluation of Capability to Deliver NO

A series of animal experiments were performed to evaluate the NO-delivering capability of different compounds. The experiments were approved by the local animal ethics committee. Male white New Zealand rabbits (n=12) were subjected to different doses of an intravenous infusion of NO-substituted solutions at different doses. Several physiological parameters were measured during the experiments, including NO concentration in mixed exhaled gas (FENO).

Anaesthesia and Initial Surgical Procedures

The animals were anaesthetised via an ear vein with sodium pentobarbital, 6 mg ml$^{-1}$ in saline, 40-60 mg kg$^{-1}$. Body temperature was maintained at 38-38.5 degrees C. by means of a heating pad connected to a thermostat. The animals were placed in supine position and tracheotomised to allow mechanical ventilation, using a constant volume ventilator (model 683, Harvard Apparatus, South Natick, Mass., USA). The ventilator was supplied with NO-free air using a charcoal filter (110×11 cm). Respiratory rate was 40 min$^{-1}$, and tidal volume was initially adjusted to keep the end-tidal $CO_2$ (ET$CO_2$) at 4.5-5.3% as determined by a gas analyser (Oscar-Oxy, Datex, Helsinki, Finland), which sampled gas (150 ml min$^{-1}$, 15-20% of minute ventilation) from one of two side-arms connected to the tracheal cannula, and using a NAPHION® sampling catheter. To the other side-arm a pressure transducer (Statham, Hato Rey, Puerto Rico) was connected to monitor the insufflation pressure (IP). The gas from the ventilator outlet was led through a switching valve to either of two beakers creating a positive end-expiratory pressure (PEEP) of 1-2 cmH$_2$O or 4-5 cmH$_2$O. During the experiment the gas flow was altered between the lower PEEP (9 min) and the higher PEEP (1 min) with an interval of totally 10 min in order to optimise ventilation and prevent atelectasis formation. A continuous infusion containing glucose (24.3 g l$^{-1}$), dextran 70 (MACRODEX® 26.5 g l$^{-1}$), NaHCO$_3$ (6.2 g l$^{-1}$), sodium pentobarbital (4.1 g l$^{-1}$) and pancuronium bromide (98 mg l$^{-1}$) was administered at a rate of 5 ml kg$^{-1}$ h$^{-1}$ via the same ear vein by means of a Terumo STC-521 syringe pump (Terumo Corp., Tokyo, Japan). A heparinised catheter was inserted in the left common carotid artery for mean blood pressure (MAP) and heart rate (HR) recordings (Statham pressure transducer), and arterial blood sampling. Another catheter was inserted in the right jugular vein for administration of infusions. The animals were allowed a 30-60 min intervention-free period to obtain stable circulatory conditions and stable FENO-values.

NO Measurements in Exhaled Breath

FENO was continuously measured by means of a chemiluminescence-based system (NIOX®, Aerocrine AB, Solna, Sweden) sampling at 100 ml min$^{-1}$ at the end of a mixing chamber connected to the ventilator exhaust. The completeness of the mixing of expired air was intermittently checked by monitoring $CO_2$ concentration in the same chamber. Calibration was performed using certified NO standard gas in nitrogen (AGA Specialgas, Lidingö, Sweden).

Preparation of NO Substituted Solutions

Different starting materials or carrier media solutions (Table 1) were dissolved and diluted with saline or water to obtain different concentration of the solutions. The solution was then placed in a gas-tight chamber and deoxygenated by means of helium bubbling for 10 min. The glass chamber was then gassed with pure nitric oxide gas for 3-4 min.

Experimental Protocol

After the stabilisation period, the animals received intravenous infusions (CMA/100, Carnegie Medicin AB, Stockholm, Sweden) of the different solutions at different infusion rates into a saline carrier flow (864 Syringe Pump, Univentor LTD, Zejtun, Malta) of 100 µl kg$^{-1}$ min$^{-1}$ through the jugular vein catheter. Blood samples were collected and analyzed for blood gases and acid-base status (ABL 300, Radiometer A/S, Copenhagen, Denmark) intermittently. FENO, ET$CO_2$, HR, MAP and IP were continuously monitored on a Grass Polygraph (Grass Instruments Co, Quincy, Mass., USA) during the experiments.

Drugs

Heparin (Kabi Vitrum, Stockholm, Sweden), pancuronium bromide (PAVULON®, Organon, Oss, Holland), dextran 70 (MACRODEX®, Pharmalink, Spånga, Sweden) and sodium pentobarbital (Apoteksbolaget) were purchased from Apoteksbolaget, Stockholm, Sweden. The other chemicals were from Sigma Chemical Co, St Louis, Mo., USA.

Statistical Analysis

Data are given as mean±SEM.

TABLE 1

Artificially-ventilated pentobarbital anesthetised rabbits (n = 1-4).

| Carrier | Concentration (M) | Dose (mmol kg$^{-1}$ min$^{-1}$) | Pre-infusion values | Infusion values | Change (absolute value) | Change (%) | Number of animals |
|---|---|---|---|---|---|---|---|
| Saline | 0.153 | 0.0153 | | | | | 2 |
| Exhaled NO (ppb) | | | 11.7 | 11.7 | 0 | 0 | |

TABLE 1-continued

Artificially-ventilated pentobarbital anesthetised rabbits (n = 1-4).

| Carrier | Concentration (M) | Dose (mmol kg$^{-1}$ min$^{-1}$) | Pre-infusion values | Infusion values | Change (absolute value) | Change (%) | Number of animals |
|---|---|---|---|---|---|---|---|
| MAP (cmH$_2$O) | | | 96.1 | 87.2 | −8.9 | −7.8 | |
| Glucose (60%) | 3.33 | 0.333 | | | | | 2 |
| Exhaled NO (ppb) | | | 15.5 | 21.7 | 6.3 | 40 | |
| MAP (cmH$_2$O) | | | 100 | 47.5 | −52.5 | −51 | |
| Fructose (60%) | 3.33 | 0.333 | | | | | 1 |
| Exhaled NO (ppb) | | | 14.9 | 28.0 | 13.1 | 88 | |
| MAP (cmH$_2$O) | | | 115.2 | 59.1 | −56.1 | −49 | |
| Galactose (60%) | 3.33 | 0.333 | | | | | 1 |
| Exhaled NO (ppb) | | | 7.9 | 11.2 | 3.3 | 41 | |
| MAP (cmH$_2$O) | | | 142.4 | 72.7 | −69.7 | −48.9 | |
| Glucosamine | 3.33 | 0.333 | | | | | 1 |
| Exhaled NO (ppb) | | | 10.3 | 9.3 | −0.9 | −9 | |
| MAP (cmH$_2$O) | | | 125.7 | 121.2 | −4.5 | −4 | |
| Arginine | 2.0 | 0.2 | | | | | 1 |
| Exhaled NO (ppb) | | | 21.2 | 21.8 | 0.6 | 3 | |
| MAP (cmH$_2$O) | | | 111.8 | 102.9 | −8.8 | −8 | |
| Sorbitol (60%) | 3.33 | 0.333 | | | | | 1 |
| Exhaled NO (ppb) | | | 7.0 | 11.2 | 4.2 | 60 | |
| MAP (cmH$_2$O) | | | 130.3 | 66.7 | −63.6 | −48.8 | |
| Mannitol (20%) | 1.11 | 0.111 | | | | | 1 |
| Exhaled NO (ppb) | | | 8.4 | 13.1 | 4.7 | 55.6 | |
| MAP (cmH$_2$O) | | | 127.3 | 66.7 | −60.6 | −48 | |
| Glucuronic acid | 3.33 | 0.333 | | | | | 1 |
| Exhaled NO (ppb) | | | 12.5 | 12.5 | 0 | 0 | |
| MAP (cmH$_2$O) | | | 82.4 | 64.7 | −17.6 | −21 | |
| Fucose | 0.609 | 0.0609 | | | | | 1 |
| Exhaled NO (ppb) | | | 18.8 | 22.9 | 4.1 | 22 | |
| MAP (cmH$_2$O) | | | 91.2 | 58.9 | −32.4 | −35 | |
| Ribose (50%) | 3.33 | 0.333 | | | | | 2 |
| Exhaled NO (ppb) | | | 12.1 ± 2.8 | 20.3 ± 0.2 | 8.2 ± 3.0 | 77 ± 43 | |
| MAP (cmH$_2$O) | | | 118.2 | 69.7 | −48.5 | −41 | |
| 2-deoxy-Ribose | 3.33 | 0.333 | | | | | 1 |
| Exhaled NO (ppb) | | | 12.1 | 44.8 | 32.7 | 269 | |
| MAP (cmH$_2$O) | | | 115.2 | 48.5 | −66.7 | −57.9 | |
| 1-O-methyl-Ribose | 3.33 | 0.333 | | | | | 1 |
| Exhaled NO (ppb) | | | 12.1 | 168 | 155.9 | 1284 | |
| MAP (cmH$_2$O) | | | 100.0 | 50.0 | −50.0 | −50 | |
| N-Acetylcysteine | 1.23 | 0.123 | | | | | 1 |
| Exhaled NO (ppb) | | | 21.2 | 25.3 | 4.1 | 19 | |
| MAP (cmH$_2$O) | | | 102.9 | 73.5 | −29.4 | −29 | |
| Glycerol | 3.33 | 0.333 | | | | | 4 |
| Exhaled NO (ppb) | | | 14.1 ± 1.3 | 77.4 ± 9.8 | 63.3 ± 10.5 | 475 ± 120 | |
| MAP (cmH$_2$O) | | | 110.3 ± 9.7 | 66.5 ± 6.8 | −43.7 ± 11.9 | −38 ± 7.7 | |
| 1,2-Propanediol (propylene glycol) | 3.33 | 0.333 | | | | | 1 |
| Exhaled NO (ppb) | | | 12.9 | 40.7 | 27.9 | 217 | |
| MAP (cmH$_2$O) | | | 94.1 | 79.4 | −14.7 | −16 | |
| 1,3-Propanediol | 3.33 | 0.333 | | | | | 1 |
| Exhaled NO (ppb) | | | 13.9 | 92.1 | 78.2 | 562 | |
| MAP (cmH$_2$O) | | | 114.7 | 76.5 | −38.2 | −33 | |
| 1-Propanol | 3.33 | 0.333 | | | | | 1 |
| Exhaled NO (ppb) | | | 12.9 | 107.1 | 94.3 | 733 | |
| MAP (cmH$_2$O) | | | 92.6 | 82.4 | −10.3 | −11 | |
| 2-Propanol | 3.33 | 0.333 | | | | | 1 |
| Exhaled NO (ppb) | | | 12.9 | 192.9 | 180 | 1400 | |
| MAP (cmH$_2$O) | | | 98.5 | 83.8 | −14.7 | −15 | |
| Alanine | 1.11 | 0.111 | | | | | 1 |
| Exhaled NO (ppb) | | | 20.8 | 20.8 | 0 | 0 | |
| MAP (cmH$_2$O) | | | 97.1 | 97.1 | 0 | 0 | |
| 2-Amino-1,3-propanediol | 3.33 | 0.333 | | | | | 1 |
| Exhaled NO (ppb) | | | 17.3 | 19.6 | 2.4 | 14 | |
| MAP (cmH$_2$O) | | | 77.9 | 64.7 | −13.2 | −17.0 | |
| 3-Amino-1,2-propanediol | 3.33 | 0.333 | | | | | 1 |
| Exhaled NO (ppb) | | | 20.2 | 20.2 | 0 | 0 | |
| MAP (cmH$_2$O) | | | 73.5 | 73.5 | 0 | 0 | |
| Lactate | 3.33 | 0.333 | | | | | 1 |
| Exhaled NO (ppb) | | | 16.7 | 16.7 | 0 | 0 | |
| MAP (cmH$_2$O) | | | 88.2 | 86.8 | −1.5 | −2 | |
| Etanol | 3.33 | 0.333 | | | | | 1 |
| Exhaled NO (ppb) | | | 17.1 | 17.1 | 0 | 0 | |
| MAP (cmH$_2$O) | | | 82.4 | 82.4 | 0 | 0 | |
| Glycine | 1.23 | 0.123 | | | | | 1 |

TABLE 1-continued

Artificially-ventilated pentobarbital anesthetised rabbits (n = 1-4).

| Carrier | Concentration (M) | Dose (mmol kg$^{-1}$ min$^{-1}$) | Pre-infusion values | Infusion values | Change (absolute value) | Change (%) | Number of animals |
|---|---|---|---|---|---|---|---|
| Exhaled NO (ppb) | | | 16.2 | 15.6 | −0.6 | −4 | |
| MAP (cmH$_2$O) | | | 105.9 | 108.8 | 2.9 | 3 | |
| Sucrose (60%) | 1.67 | 0.167 | | | | | 1 |
| Exhaled NO (ppb) | | | 14.9 | 26.1 | 11.2 | 75 | |
| MAP (cmH$_2$O) | | | 127.3 | 71.2 | −56.1 | −44 | |
| Lactobionic acid | 1.11 | 0.111 | | | | | 1 |
| Exhaled NO (ppb) | | | 19.6 | 28.0 | 8.3 | 42 | |
| MAP (cmH$_2$O) | | | 91.2 | 58.8 | −32.4 | −35 | |
| Polyethylene glycol | 3.33 | 0.333 | | | | | 1 |
| Exhaled NO (ppb) | | | 18.2 | 29.4 | 11.2 | 61 | |
| MAP (cmH$_2$O) | | | 91.2 | 73.5 | −17.6 | −19 | |
| Inulin (15%) | 0.03 | 0.003 | | | | | 1 |
| Exhaled NO (ppb) | | | 14.9 | 16.7 | 1.8 | 12 | |
| MAP (cmH$_2$O) | | | 85.3 | 58.8 | −26.5 | −31 | |
| Dextran (15%) | 0.00093 | 0.000093 | | | | | 1 |
| Exhaled NO (ppb) | | | 11.7 | 14.5 | 2.8 | 24 | |
| MAP (cmH$_2$O) | | | 131.8 | 86.4 | −45.5 | −34 | |
| Heparin (15000 IU/ml, 10%) | 0.0056 | 0.00056 | | | | | 1 |
| Exhaled NO (ppb) | | | 12.5 | 11.9 | −0.6 | −5 | |
| MAP (cmH$_2$O) | | | 72.1 | 63.2 | −8.8 | −12 | |
| Fucoidan (10%) | | | | | | | 1 |
| Exhaled NO (ppb) | | | 20.6 | 25.3 | 4.7 | 23 | |
| MAP (cmH$_2$O) | | | 107.4 | 51.5 | −55.9 | −52 | |
| Albumin (20%) | | | | | | | 1 |
| Exhaled NO (ppb) | | | 16.2 | 16.7 | 0.6 | 4 | |
| MAP (cmH$_2$O) | | | 105.9 | 73.5 | −32.4 | −31 | |

Changes in mixed exhaled nitric oxide and mean arterial blood pressure (MAP) due to intravenous infusion (100 μL/kg$^{-1}$ min$^{-1}$) of different carrier solutions saturated with pure nitric oxide gas.

The results show that many of the tested compounds function as a source of NO and support the generalizations presented in the claims. Compared to the saline control, glucose, fructose, galactose, ribose, sorbitol, mannitol, fucose, 2-deoxy-ribose, 1-O-methyl-ribose, sucrose, lactobionic acid, inulin, dextran, fucoidan, 1-propanol, 2-propanol, 1,2-propanediol (propylene glycol), 1,3-propanediol, glycerol, polyethylene glycol, N-acetyl-cysteine, and albumin exhibited a noticeable effect.

When unsubstituted L-cysteine was deoxygenated and exposed to NO gas, a copious precipitate, unsuitable for infusion, was formed.

When short chain alcohols were tested, a marked effect was recorded for 1-propanol and 2-propanol. Also the compounds 1,2-propanediol and 1,3-propanediol exhibited NO delivering capacity in the experiments.

Further, the results obtained with sucrose, inulin, dextran and fucoidan indicate that the invention is applicable to polymeric compounds.

3. Evaluation of Propanediol-NO and Glycerol-NO in a Pulmonary Hypertension Model Anaesthesia and Surgical Procedures The experiments were approved by the local animal ethics committee. Male white New Zealand rabbits (n=2) were anaesthetised and prepared and examined for exhaled NO as in Example 2. A continuous infusion containing glucose (25.9 g l$^{-1}$), dextran 70 (Macrodex®, 28.2 g l$^{-1}$), NaHCO3 (6.6 g l$^{-1}$), sodium pentobarbital (2.1 g l$^{-1}$), and pancuronium bromide (Pavulon®, 40 mg l$^{-1}$) was administered at a rate of 10 ml kg$^{-1}$ h$^{-1}$ via the ear vein by means of a Terumo STC-521 syringe pump (Terumo Corp., Tokyo, Japan). A heparinised catheter was inserted in the left common carotid artery for mean arterial blood pressure and heart rate recordings (Statham pressure transducer), and arterial blood sampling. Another catheter was inserted in the right jugular vein for administration of drugs. A mid thoracotomy was done and a flow probe (connected to a T201 2-channel ultrasonic blood flow meter, Transonic Systems Inc.) was placed around the ascending aorta to measure cardiac output. One catheter was introduced via the right ventricle wall and put into the pulmonary artery for measurement of pulmonary artery pressure by means of a Uniflow pressure transducer (Baxter). Another catheter was inserted in the left atrium via the left atrial wall and the left atrial pressure was measured with a pressure transducer (Statham, Hato Rey, Puerto Rico). During the experiment there was a low flow (3 ml h$^{-1}$) of physiological saline by means of a syringe pump (Perfusor Secure, B. Braun Melsungen AG, Germany) through these catheters to prevent clotting. Pulmonary vascular resistance was calculated with the common formula. After the surgery, the animals were allowed a 30-60 min intervention-free period to reach stable circulatory conditions and FENO values.

Preparation of NO Solutions 1,2-propanediol was dissolved to a 25% (v/v) solution in water and glycerol was dissolved to a 25% (v/v) solution in water and placed in gas-tight cylinders. The solutions were deoxygenated by helium bubbling during 10 min and then treated with pure nitric oxide gas for 3 min. From the gas-tight cylinders the solutions were transferred to syringes for i.v. infusions.

Experimental Protocol

In both animals, pulmonary hypertension was induced by means of an intravenous infusion (CMA/100, Carnegie Medicin AB, Stockholm, Sweden) of a thromboxane receptor agonist U46619 (9,11-Dideoxy-11α,9α-epoxymethanoprostaglandin F2α; Larodan Fine Chemicals AB, Malmo, Sweden). The stock solution was 10 mg ml$^{-1}$ in MH 55669-33-methyl acetate and before infusion it was diluted in physiological saline to 10 μg ml$^{-1}$. The U46619-solution was infused (30 μl kg$^{-1}$ min$^{-1}$) into the carrier flow of 100 ml min$^{-1}$ in the jugular vein catheter to increase the pulmonary arterial pressure to approximately 40 cmH$_2$O and this infusion was continuous throughout the experiment. The two animal received glycerol-NO infusions or 1,2-propanediol-NO infusions in different doses (10, 30 and 100 µl kg$^{-1}$ min$^{-1}$) during the U446619 infusion in order to investigate the ability of the NO-solutions to counteract pulmonary hypertension. The NO solution was infused by means of an infusion pump (CMA/100, Carnegie Medicin AB, Stockholm, Sweden) into the saline carrier flow through the jugular vein catheter. Arterial blood samples were collected and analysed for blood gases and acid-base status (ABL 300, Radiometer A/S, Copenhagen, Denmark) intermittently during the experiments. Respiratory and hemodynamic parameters were continuously monitored on a Grass Polygraph (Grass Instruments Co, Quincy, Mass., USA) during the experiments.

Drugs

The drugs purchased were: Heparin (Kabi Vitrum, Stockholm, Sweden), pancuronium bromide (Pavulon®, Organon, Oss, Holland), dextran 70 (Macrodex, Pharmalink, Spånga, Sweden) and sodium pentobarbital (Apoteksbolaget, Stockholm, Sweden). Routine chemicals were from Sigma Chemical Co (St Louis, Mo., USA).

Results

Glycerol-NO and 1,2-propanediol-NO infusions attenuated the U46619-induced pulmonary hypertension in a dose-dependent manner (FIGS. 8 and 9) and the highest dose (100 µl kg$^{-1}$ min$^{-1}$) almost normalised pulmonary vascular resistance.

4. Evaluation of Glycerol-NO in a Pulmonary Embolism Model Methods

Anaesthesia and Surgical Procedures

The experiments were approved by the local animal ethics committee. Male white New Zealand rabbits (n=4) were anaesthetised and prepared and examined for exhaled NO as in Example 3. A catheter was inserted in the right jugular vein for administration of drugs and pulmonary emboli material. A mid thoracotomy was done and a flow probe (connected to a T201 2-channel ultrasonic blood flow meter, Transonic Systems Inc.) was placed around the ascending aorta to measure cardiac output. Heparinised catheters were placed in the pulmonary artery via the left jugular vein and in the left atrium for measurement of pulmonary artery pressure (Statham pressure transducer, Statham, Hato Rey, Puerto Rico) and left atrial pressure (Statham, supra) respectively. Pulmonary vascular resistance was calculated with the common formula. Muscles from the anterior compartment of the right lower hind limb were resected and placed in saline. After the surgery, the animals were allowed a 30-60 min intervention-free period to reach stable circulatory conditions and FENO values.

Preparation of NO Solutions

Glycerol was dissolved to a 25% (v/v) solution in water and placed in gas-tight cylinders. The solution was deoxygenated by helium bubbling during 10 min and the treated with pure nitric oxide gas for 3 min. From the gas-tight cylinders the solution was transferred to syringes for i.v. infusions.

Preparation of Muscle Emboli

Material for muscle tissue pulmonary embolisation (MPE) was prepared by modification of a technique described previously. Thus, resected anterior tibial skeletal muscle was cleared from visible connective tissue and then homogenized and dissolved in normal saline to a concentration of 0.1 g muscle ml$^{-1}$ and 50 IE heparin ml$^{-1}$ was added to the mixture. The homogenate was passed through a 0.5-mm mesh to prevent obstruction in the three-way stopcock of the venous catheter.

Experimental Protocol

In all groups, pulmonary embolism was induced by means of an intravenous infusion (CMA/100, Carnegie Medicin AB, Stockholm, Sweden) of MPE material (300 µl kg$^{-1}$, i.e. 30 mg kg$^{-1}$) at a flow of 150 µl kg$^{-1}$ min$^{-1}$ into a carrier flow (864 Syringe Pump, Univentor LTD, Zejtun, Malta) of 150 µl kg$^{-1}$ min$^{-1}$. Three animals did not receive any treatment (control group) whereas one animal received an intravenous infusion of glycerol-NO (100 µl kg$^{-1}$ min$^{-1}$) for 30 min, starting 20 min after the pulmonary embolisation. The NO solution was infused by means of an infusion pump (CMA/100, Carnegie Medicin AB, Stockholm, Sweden) into a saline carrier flow (864 Syringe Pump, Univentor LTD, Zejtun, Malta) of 100 ml min$^{-1}$ through the jugular vein catheter. Arterial blood samples were collected and analysed for blood gases and acid-base status (ABL 300, Radiometer A/S, Copenhagen, Denmark) intermittently during the experiments. Respiratory and hemodynamic parameters were continuously monitored on a Grass Polygraph (Grass Instruments Co, Quincy, Mass., USA) during the experiments.

Drugs

The drugs purchased were: Heparin (Kabi Vitrum, Stockholm, Sweden), pancuronium bromide (Pavulon®, Organon, Oss, Holland), dextran 70 (Macrodex, Pharmalink, Spånga, Sweden) and sodium pentobarbital (Apoteksbolaget, Stockholm, Sweden). Routine chemicals were from Sigma Chemical Co (St Louis, Mo., USA).

Results

Induction of pulmonary embolism increased the pulmonary vascular resistance to a similar level in all animals. Infusion of glycerol-NO clearly decreased pulmonary vascular resistance in the treated animal, showing the potential of the NO solutions in decreasing pulmonary hypertension in pulmonary embolism. See FIG. 10.

5. Myocardial Ischemia-reperfusion Injury

Anaesthesia and Surgical Procedures

The experiments were approved by the local animal ethics committee. Male white New Zealand rabbits (n=10) were anaesthetised and prepared and examined for exhaled NO as in Example 3. A continuous infusion containing glucose (25.9 g l$^{-1}$), dextran 70 (Macrodex®, 28.2 g l$^{-1}$), NaHCO$_3$ (6.6 g l$^{-1}$), and sodium pentobarbital (3.1 g l$^{-1}$) was administered at a rate of 7.5 ml kg$^{-1}$ h$^{-1}$ via the ear vein by means of a Terumo STC-521 syringe pump (Terumo Corp., Tokyo, Japan): A heparinised catheter was inserted in the left femoral artery for mean arterial blood pressure and heart rate recordings (Statham pressure transducer), and arterial blood sampling. Another a catheter was inserted in the right jugular vein for administration of drugs. A heparinised catheter was placed in the left ventricle via the left common carotid artery for measurement of left ventricular pressure (Statham pressure transducer) and on-line calculation of left ventricular dP/dt. A surface ECG showing lead II was displayed during the experiments. A left thoracotomy was done via the fourth intercostal space, and a coronary ligature was placed around a large anterior descending branch of the circumflexa artery on the left ventricular wall approximately 1 cm from the base of the heart with surgical suture material (5-0 Vicryl®, ETHICON, manufacturer Johnson & Johnson Jutl, Brussels, Belgium). A coronary snare which could be tightened and loosened was created with the ligature and a PE tube. After the surgery, the animals were allowed a 30-60 min intervention-free period to reach stable circulatory conditions and FENO values.

Preparation of NO Solutions 1,2-propanediol was dissolved to a 25% (v/v) solution in water and D-glucose was dissolved in water (60%, w/v) and placed in gas-tight cylinders. The solutions were deoxygenated by helium bubbling during 10 min and then treated with pure nitric oxide gas for 3 min. From the gas-tight cylinders the solutions were transferred to syringes for i.v. infusions.

Experimental Protocol

In all groups, the coronary snare was tightened after the intervention-free period to induce ischemia which was confirmed with ST-elevations on the ECG. After 30 min of ischemia the coronary snare was reopened to start 120 min of reperfusion and then the experiments were finished. The animals were divided into three groups: (1) control, (2) treatment with i.v. infusion of 30 μl $kg^{-1}$ $min^{-1}$ glucose-NO starting at 15 min of ischemia and stopped after 60 min of reperfusion, (3) treatment with i.v. infusion of 10 μl $kg^{-1}$ $min^{-1}$ 1,2-propanediol-NO starting after 15 min of ischemia and stopped after 120 min of reperfusion. The NO solutions was infused by means of an infusion pump (CMA/100, Carnegie Medicin AB, Stockholm, Sweden) into a saline carrier flow (864 Syringe Pump, Univentor LTD, Zejtun, Malta) of 100 ml $min^{-1}$ through the jugular vein catheter. Arterial blood samples were collected and analysed for blood gases and acid-base status (ABL 300, Radiometer A/S, Copenhagen, Denmark) intermittently during the experiments. Respiratory and hemodynamic parameters, and the lead II of the ECG were continuously monitored and collected at a rate of 1000 Hz per channel by means of a computer-based acquisition system (Biopac, BIOPAC Systems Inc., Goleta, Calif., USA) during the experiments.

Arrhythmia Analysis

After the experiments the groups were analysed with respect to arrhythmias during the reperfusion. Every minute of the reperfusion was searched for arrhythmic heart beats and if a certain minute contained such a beat this minute was defined as an arrhythmic minute. These arrhythmic minutes were summed during the reperfusion to yield accumulated arrhythmic minutes in each group and then normalised to the sample size of each group.

Drugs

The drugs purchased were: Heparin (Kabi Vitrum, Stockholm, Sweden), dextran 70 (Macrodex, Pharmalink, Spånga, Sweden) and sodium pentobarbital (Apoteksbolaget, Stockholm, Sweden). Routine chemicals were from Sigma Chemical Co (St Louis, Mo., USA).

Results

Reperfusion induced arrhythmias in all groups. However, treatment with either glucose-NO (n=3) or 1,2-propanediol-NO (n=3) clearly reduced the incidence of arrhythmias compared to controls (n=4) as can be seen in FIG. 11.

6. Chemical Analysis of Reaction Products from the Interaction Between NO and Hydroxyl Containing Compounds (Alcohols, Sugars)

All reaction mixtures and dilutions of standards were prepared in glass cylinders equipped with TEFLON® coated rubber septa for injection of reactants and sampling respectively.

HPLC

Analysis of reaction mixtures and commercial organic nitrites and nitrates was made by high performance liquid chromatography (HPLC) using reverse phase chromatography on C8, C18 or CN columns (Waters Inc. NOVAPAK™ 4 μm particle size 8×100 mm radial compression columns) by means of two LDC Constametric pumps delivering a constant total flow of 1 ml per min, controlled by a computerized gradient control system generating a linear gradient of 0-100% methanol (elution solvent B) in 33 min, starting 1 min after injecting sample in the aqueous initial elution solvent (solvent A) which contained 5 mM ammonium formiate at pH 6. Separation of eluted compounds was determined by an LDC Spectromonitor variable UV monitor set at 210 nm, followed by a Pharmacia Wavescan wavelength scanning detector producing UV scans between 190 and 370 nm at 4 s intervals which were stored on a computer and analyzed after each HPLC run. The output from the LDC Spectromonitor was continuously recorded on a strip chart recorder.

Injections of reaction mixtures were made at 2.5-100 ul via a Rheodyne injector equipped with a 2 ml loop. For collection of peaks for further analysis by gas chromatography-mass spectrometry (GC-MS) repeated injections were made, up to 10 ml of reaction mixture, before the gradient of A to B was started. Fractional sampling was made anaerobically by a 3-way stopcock with Luer connectors connected to the elution flow immediately after the Wavescan detector. Glass syringes were used to collect the eluent to prevent entry of air into the collected sample, which was sealed off by closing the stopcock after the respective eluting compound, as determined by peaks in the 210 nm recording, had eluted.

In a few experiments an Agilent 1100 chromatography system with Agilent binary pumps+diode array detector system was used with a Thermo 3 um C18 column (2.1×100 mm) for analysis of reaction products. The solvent flow was 0.5 ml per min, and elution solvent A was 2 mM ammonium acetate. A gradient to 100% methanol was run in 15 min. Anaerobic sampling was performed of eluting compounds as above.

GC-MS

Extracted samples experiments: Eluted peaks were extracted by an equal volume of toluene in a small sealed sample vial, shaken briefly, and quickly separated by centrifugation, if necessary. The toluene phase was placed in an autosampler vial and 1 ul fractions were injected onto an Agilent DB-5MS (0.25 mm i.d., 30 m length, inner coating: 95% methylsilicone and 5% phenyl) gas chromatography column at an initial temperature of 40 degrees C., whereafter the column temperature was raised by 10 degrees C. per min until a temperature of 200 or 250° C. was reached. Detection of eluted compounds was made by a Hewlett Packard 5973 Mass Selective Detector (quadrupole MS). The gas chromatograph was a Hewlett Packard 6890 Series GC system with a Hewlett Packard Enhanced Parameters Injector system. Data were collected and analyzed with an Enhanced Chemstation G1701 BA computer program with a Wiley 7n library of mass spectra.

Direct injection experiment: In one experiment direct injections of 1 microliter of reaction mixture consisting of approx 100% propanol and NO gas were made by injection directly onto the gas chromatography column, by means of a gas tight microsyringe, bypassing the extraction procedure and the autosampling system. Commercial propyl nitrite was diluted in toluene and injected the same way for comparison.

Further Analysis, Including Chemical Ionization

Samples of 1,2-propanediol 25% or approximately 100% were treated with NO gas, and injected in the GC-MS system, now equipped with an Agilent DB-1701 column, at 0.5 microliter in a total He flow of 30 ml per min, split fraction 1:20. Temperature gradient was as above. Mass spectrometry was either performed in electron impact (EI) mode, or in chemical ionisation mode (CI) using a chemical ionisation interface supplied with a methane flow.

Results of Chemical Analysis

HPLC: On all three Novapak columns and on the Thermo column a single peak of product, from the reaction between propanol and NO gas, eluted at a gradient concentration of 70-80% methanol. In the NOVAPAK C18 system this corresponded to an elution time of approximately 28 min (FIG. 12, panel C). The 28 min peak had a single UV absorbance max at 225 nm in the HPLC eluent, as determined by the Wavescan detector. When a standard sample of propyl nitrite (Karl Industries Inc., Aurora, Ohio, USA) diluted in a gas-type cylinder in deoxygenated (10 min He purging) water at 1:1000 was injected, a small peak at 28 min was obtained (FIG. 12, panel A), having an identical UV absorbance max at 225 nm. The 28 min peak was 5-10 times larger if the dilution of propyl nitrite was made in water saturated with NO gas (FIG. 12, panel B), still exhibiting the same UV characteristics. Similar results were obtained on the C8 and CN columns, a single retained peak was obtained from the reaction mixture consisting of propanol and NO, although at somewhat shorter retention times, compared with the C18 system. Propyl nitrite commercial sample also in these systems produced a peak coinciding with the propanol+NO reaction product retention time, and exhibiting the same UV characteristics as above, but being smaller in size. A commercial sample of propyl nitrate was also studied for reference in the CN column HPLC system, and had an elution time which significantly differed from the propyl nitrite elution time and did not coincide with the 28 min peak or any other peak in propanol-NO or propyl nitrite chromatograms.

HPLC purified and extracted samples analysed by GC-MS: When the 28 min peak from the C18 HPLC chromatography was sampled, extracted in toluene, and injected on the GC-MS system several peaks eluted. At the front (1.5 min) the expected air gas peaks (e.g. $CO_2$ and oxygen-18 were observed, together with a NO peak. At 3 min a peak exhibiting mass spectral characteristics for propyl nitrite was identified by the MS. Propanol was eluted and identified at 3.5 min in the GC-MS system, followed by small amounts of benzene (breakdown product of toluene) at 5.5 min, and then a large toluene peak at 8 min.

Direct injection for GC-MS analysis: Direct on-column injection of commercial propyl nitrite confirmed the elution time (3 min) and mass spectral characteristics of propyl nitrite observed in the extracted peak from the propanol+NO gas reaction mixture, eluted and collected at 28 min in the C18 HPLC. Direct on-column injection of propanol+NO gas mixture, obtained from the gas-tight reaction vessel, immediately diluted in deaerated toluene and injected onto the GC-MS contained an initial peak of NO gas at the elution front, propyl nitrite at 3 min, and a very large peak of propanol eluting from 3.2 min and several minutes thereafter, followed by toluene (FIG. 13).

In conclusion, propyl nitrite was identified in propanol+ NO gas mixtures both by HPLC, by comparison with a commercial standard, and by GC-MS either by analysis of purified peaks from HPLC runs or after direct injection of propanol+NO gas reaction mixture onto the GC-MS system.

Further analysis by GC-MS: Propanediol and propanediol-NO was similarly analysed, using automated injection on an Agilent DB-1701 column. The results shown in FIGS. 14, 15a and 15b support the hypothesis that the reaction mixture following the method according to the invention comprises the two isoforms of 1,2-propandiyl nitrite and unreacted propanediol. FIG. 14 b shows that the main abundance of mass fragment 30, a common fragment for organic nitrites, was found in the 2 chromatographic peaks for compound 1 and 2. Mass spectrometry using chemical ionization, shown in FIGS. 16a and b, demonstrated the M−1 and M+1 molecular ions in the mass spectra for both compound 1 and 2, as should be expected from the structures shown with the mass spectra in FIGS. 15a and b.

Comparison Between Reaction Mixtures with Other Alcohols and NO Versus Commercial Samples of Organic Nitrites Commercial samples of ethyl nitrite, butyl nitrite, and isobutyl nitrite (Sigma-Aldrich) were diluted anaerobically as above and injected onto the HPLC system, using either the Novapak C8 or CN column. Peaks with UV absorbance maxima of approximately 225 nm were obtained in all the samples, but at different retention times corresponding to the expected differences judged from the lipophilic chain length of the compounds. All these peaks were larger if the dilution of the organonitrite had been done in de-aerated NO saturated solutions. The respective peaks with UV max at 225 nm coincided with single similar peaks obtained by treating the corresponding alcohol (ethanol, butanol, isobutanol) with NO gas. This was taken as evidence that the corresponding organic mononitrite had formed.

Analysis by HPLC of Glucose, Sucrose and Glycerol Reaction Products with NO Gas

When glucose, glycerol or sucrose solutions 25-100% (weigh/vol) in water were de-aerated and treated with NO gas several peaks were identified in HPLC chromatograms by reversed phase chromatography. Some of these peaks exhibited the 225 nm UV absorbance characteristics suggesting that organic nitrite ester had been formed.

Verification of NO donating capacity in alcohol-NO and sugar-NO reaction products:

Samples of eluents from the HPLC system were collected and analyzed for NO/nitrite content by injection into a reaction vessel containing 1% sodium iodide in hot acetic acid. Released nitric oxide was purged into a chemiluminescence analyzer system optimized for detection of nitric oxide by chemiluminescence reaction with ozone and determination of NO+ozone-generated excited $NO_2$ product through counting of emitted photons.

Results

The reaction products identified as retained peaks in HPLC from treatment of glucose and propanol were all shown to yield NO by this relatively mild reduction treatment. Nitroglycerin (glyceryl trinitrate) did not yield a release of NO under these conditions, confirming that the reaction mixture between glycerol and NO contained an organic nitrite rather than an organic nitrate.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

REFERENCES

Abman S H, Chaffield B A, Hall S L & McMurtry I F (1990). Role of endothelium-derived relaxing factor during transition of pulmonary circulation at birth. Am J Physiol. 259: H1921-7

Cederqvist B. et al., Direct demonstration of NO formation in vivo from organic nitrites and nitrates, and correlation to effects on blood pressure and to in vitro effects, Biochemical Pharmacology, Vol. 47, No. 6, pp. 1047-1053, 1994.

Gustafsson L E, Leone A M, Persson M G, Wiklund N P & Moncada S (1991). Endogenous nitric oxide is present in the exhaled air of rabbits, guinea pigs and humans. Biochem Biophys Res Commun. 181:852-7.

Heymann M A (1999). Control of the pulmonary circulation in the fetus and during the transitional period to air breathing. Eur J Obstet Gynecol Reprod Biol. 84: 127-32

Larsen et al., Effects of dietary nitrate on blood pressure in healthy volunteers, N Engl J Med 355, 2792-3 (2006)

Persson M G, Gustafsson L E, Wiklund N P, Moncada S & Hedqvist P (1990). Endogenous nitric oxide as a probable modulator of pulmonary circulation and hypoxic pressor response in vivo. Acta Physiol Scand. 140: 449-57

Rimeika D et al., Regulation of regional lung perfusion by nitric oxide, Am J Respir Crit Care Med 2004, 170(4): 450-5

Stamler J S, Loh E, Roddy M A, Currie K E & Creager M A (1994). Nitric oxide regulates basal systemic and pulmonary vascular resistance in healthy humans. Circulation. 89: 2035-40.

The invention claimed is:

1. A compound chosen among the compounds having formulas I and II below:

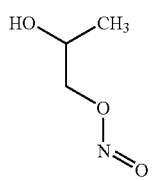

2-hydroxypropyl nitrite

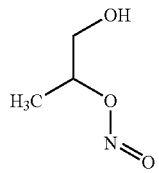

2-hydroxy-1-methylethyl nitrite wherein formula I is 2-hydroxypropyl nitrite and formula II is 2-hydroxy-1-methylethyl nitrite.

2. A therapeutic formulation comprising a physiologically acceptable and therapeutically effective composition comprising a compound according to claim 1 stored in the presence of an excess of NO.

3. A therapeutic formulation comprising a physiologically acceptable and therapeutically effective composition comprising a compound according to claim 1.

* * * * *